US012383604B2

(12) United States Patent
Mulé et al.

(10) Patent No.: US 12,383,604 B2
(45) Date of Patent: Aug. 12, 2025

(54) BIOENGINEERING TERTIARY LYMPHOID STRUCTURES USING CHITOSAN-BASED HYDROGELS

(71) Applicant: H. Lee Moffitt Cancer Center and Research Institute, Inc., Tampa, FL (US)

(72) Inventors: James Mulé, Odessa, FL (US); Rana Falahat, Tampa, FL (US); Genyuan Zhu, Columbia, SC (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 1068 days.

(21) Appl. No.: 17/052,973

(22) PCT Filed: May 8, 2019

(86) PCT No.: PCT/US2019/031306
§ 371 (c)(1),
(2) Date: Nov. 4, 2020

(87) PCT Pub. No.: WO2019/217547
PCT Pub. Date: Nov. 14, 2019

(65) Prior Publication Data
US 2021/0220441 A1    Jul. 22, 2021

Related U.S. Application Data

(60) Provisional application No. 62/668,609, filed on May 8, 2018.

(51) Int. Cl.
| A61K 38/19 | (2006.01) |
| A61K 9/00 | (2006.01) |
| A61K 35/26 | (2015.01) |
| A61K 47/36 | (2006.01) |

(52) U.S. Cl.
CPC .......... *A61K 38/195* (2013.01); *A61K 9/0024* (2013.01); *A61K 35/26* (2013.01); *A61K 38/191* (2013.01); *A61K 47/36* (2013.01)

(58) Field of Classification Search
CPC ............................ A61K 38/195; A61K 9/0024
See application file for complete search history.

(56) References Cited

U.S. PATENT DOCUMENTS

| 8,288,159 B2* | 10/2012 | Warren | C12N 5/0697 435/375 |
| 9,234,175 B2 | 1/2016 | Mule | |
| 9,522,114 B1* | 12/2016 | Alcantar | A61K 47/24 |
| 2010/0272805 A1* | 10/2010 | Singh | A61K 9/06 424/484 |
| 2015/0094518 A1* | 4/2015 | Wu et al. | A61K 45/06 |

FOREIGN PATENT DOCUMENTS

WO    WO-2018045058 A1 *   3/2018   ........... A61K 31/415

OTHER PUBLICATIONS

Kobayashi Y, Watanabe T. Gel-Trapped Lymphorganogenic Chemokines Trigger Artificial Tertiary Lymphoid Organs and Mount Adaptive Immune Responses In Vivo. Front Immunol. Aug. 2, 20162;7:316. doi: 10.3389/fimmu.2016.00316. PMID: 27597851; PMCID: PMC4992816. (Year: 2016).*
Kobayashi et al. (Front Immunol. Aug. 22, 2016:7:316.) (Year: 2016).*
International Search Report issued for PCT/US2019/031306, mailed Jul. 24, 2019.
Kobayashi et al., Gel-Trapped Lymphorganogenic Chemokines Trigger Artificial Tertiary Lymphoid Organs and Mount Adaptive Immune Responses In Vivo, Front Immunol, vol. 7, No. 316, p. 1-10, 2016.
Williams-Abbott et al., The Lymphotoxin-α (LTα) Subunit is Essential for the Assembly, but Not for the Receptor Specificity, of the Membrane-anchored LTα1ß2 Heterotrimeric Ligand, The Journal of Biological Chemistry, vol. 272, No. 31, Issue of August 1, p. 19451-19456, 1997.
Messina et al., 12-Chemokine Gene Signature Identifies Lymph Node-like Structures in Melanoma: Potential for Patient Selection for Immunotherapy?, Scientific Reports, 2:765, 1-6, 2012.

* cited by examiner

Primary Examiner — Fereydoun G Sajjadi
Assistant Examiner — Joel D Levin
(74) Attorney, Agent, or Firm — Thomas | Horstemeyer, LLP

(57) ABSTRACT

As disclosed herein, stromal cells are important for the recruitment and organization of lymphocytes in TLSs. Therefore, disclosed herein are composition and methods for bioengineering TLSs in animals, such as mice. These compositions involve chemokine-releasing microparticles or cells that can be implanted into the animals. Therefore, disclosed herein are chitosan hydrogels with chemokine releasing microparticles or cells.

8 Claims, 38 Drawing Sheets

Residual Part

Hydrogel

1.F3 Stromal + Chitosan – Day 8

BIOENGINEERING TERTIARY LYMPHOID STRUCTURES USING CHITOSAN-BASED HYDROGELS

CROSS-REFERENCE TO RELATED APPLICATIONS

This application is a National Stage of International Application No. PCT/US2019/031306, filed May 8, 2019, which claims benefit of U.S. Provisional Application No. 62/668,609, filed May 8, 2019, which is hereby incorporated herein by reference in its entirety.

STATEMENT REGARDING FEDERALLY SPONSORED RESEARCH OR DEVELOPMENT

This invention was made with Government Support under Grant Nos. CA148995, CA184845, CA076292, and CA 168536 awarded by the National Institutes of Health. The Government has certain rights in the invention.

BACKGROUND

Tertiary lymphoid structures (TLSs) have been identified in various tumor types including breast, lung, melanoma and colorectal cancers, and are generally predictor of a favorable clinical outcome. However, their development and therapeutic function have not been extensively investigated, partially due to the lack of appropriate mouse models. To create such models, we developed injectable chitosan-based hydrogels embedded with chemokine-releasing microparticles or stromal cells and examined their potential for inducing TLSs in mice.

SUMMARY

As disclosed herein, stromal cells are important for the recruitment and organization of lymphocytes in TLSs. Therefore, disclosed herein are composition and methods for bioengineering TLSs in animals, such as mice. These compositions involve chemokine-releasing microparticles or cells that can be implanted into the subject. Therefore, disclosed herein are chitosan hydrogels with chemokine-releasing microparticles or cells.

In some embodiments, the microparticles or cells release CCL2, CCL3, CCL4, CCL5, CCL8, CCL18, CCL19, CCL21, CXCL9, CXCL10, CXCL11, CXCL13, or any combination thereof. For example, in some cases, the microparticles or cells can release CCL-19, CCL-21, CXCL-13, or any combination thereof. In some embodiments, the microparticles or stromal cells further release lymphotoxin-a2/b1.

In some embodiments, the microparticle is any biocompatible particle capable of sustained release of chemokines. In some embodiments, the microparticle is a lipid-enveloped mesoporous microparticle. In some embodiments, the microparticle is an alginate/chitosan microsphere, liposomal polymeric gel. PLGA nanoparticle, avidin-coated PLGA nanoparticle, PLGA microsphere, lipid-coated PLGA microparticle, medgel microgel, or liposome PLGA particle.

In some embodiments, the cells are stromal cells. In some embodiments, the cells are lymph node-derived stromal cells. In some embodiments, the cells are follicular helper T cells. In some embodiments, the cells are antigen pulsed dendritic cells.

Also disclosed herein is a method for bioengineering tertiary lymphoid structures (TLSs) in animals that involves administering to the animal the TLS composition disclosed herein.

Also disclosed herein is a method for treating a solid tumor in a subject that involves administering an effective amount of the TLS composition disclosed herein. For example, in some embodiments, the TLS composition is implanted into the solid tumor.

Also disclosed herein is a method for enhancing immunotherapy in a subject with a solid tumor, comprising administering to the subject an effective amount of the TLS composition to the solid tumor. For example, in some embodiments, the composition is implanted into the solid tumor. In some embodiments, the immunotherapy comprises adoptive transfer of a therapeutic lymphocyte. For example, in some embodiments, the immunotherapy comprises a checkpoint inhibitor selected from an anti-PD-1 antibody, an anti-PD-L1 antibody, an anti-CTLA-4 antibody, or a combination thereof.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic diagram of cell encapsulation in a thermosensitive chitosan hydrogel. FIG. 1B shows mouse splenocytes encapsulated in chitosan hydrogel and the control group that cultured in complete medium displayed similar viability. FIG. 1C shows human non-small cell lung cancer TILs encapsulated in chitosan hydrogel maintained their viability and continued to proliferate and formed colonies during a 21-day culture period.

FIG. 2A is a schematic illustrating preparation of lipid-enveloped MPs containing chemokine. FIG. 2B contains fluorescence microscopy images of MPs containing Alexa Fluor 488-labeled CCL-19. FIG. 2C shows kinetics of CCL-19 release from MPs measured over 7 days using ELISA and the percentage of CCL-19 released from MPs compared to the CCL-19 release at day 7. FIG. 2D contains bar graphs summarizing chemotactic assays showing chemokines encapsulated in MPs remain functional in the recruitment of mouse splenocytes.

FIG. 3A shows MPs containing CCL-19, CCL-21, CXCL-13, and lymphotoxin-a2/b1 embedded in chitosan hydrogel and injected into C57BL/6 mice. FIG. 3B contains representative photographs of induced structures and/or remaining hydrogels at week 3 post injection. FIG. 3C shows flow cytometry analysis of the hydrogels and newly formed surrounding tissue (residual part) dissected from mice at week 3. FIGS. 3D and 3E show total number of different immune cell subsets infiltrated into the structures at week 3 post injection.

FIG. 4A shows flow-cytometric analysis of 1.F3, a lymph node-derived stromal monoclonal cell line. FIG. 4B shows 1.F3 stromal cells embedded in chitosan hydrogel and injected into C57BL/6 mice. FIGS. 4C and 4D show total number of different immune cell subsets infiltrated into chitosan only, chitosan with chemokine releasing MPs and chitosan with 1.F3 stromal cells.

FIG. 5A shows expression of cell adhesion molecules VCAM-1 and ICAM-1 in 1.F3 stromal cells following treatment with α-LTbR and/or TNF-α for 24 and 48 h. FIG. 5B shows cell culture supernatants from 1.F3 cells treated with α-LTbR and/or TNF-α were used in a chemotactic assay with mouse splenocytes to assess chemotactic capacity of stimulated stromal cells.

DETAILED DESCRIPTION

Figure 1A:
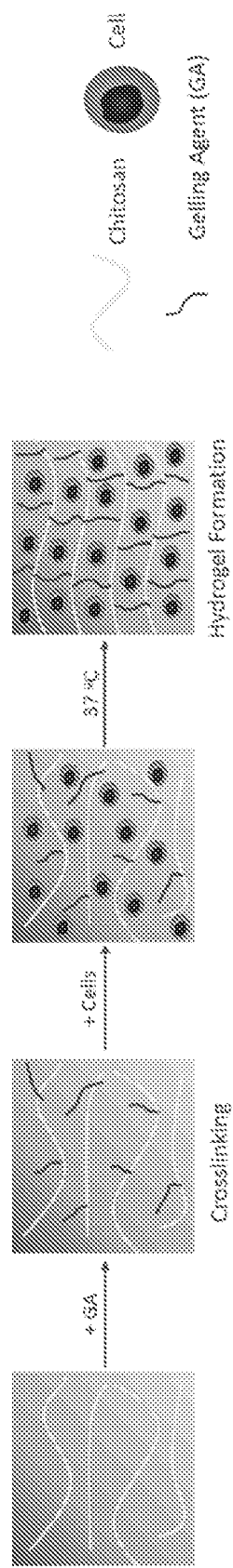
FIGS. 1A to 1C show cell viability assessment in chitosan hydrogel using LIVE/DEAD fluorescence assay.

Disclosed herein are chitosan hydrogels with chemokine-releasing microparticles or cells and their use in bioengineering TLSs in animals, such as mice.

Chemokines

In some embodiments, the disclosed hydrogels release at least one exogenous chemokines. Chemokines, which are small protein molecules involved in immune and inflammatory responses, direct leukocyte trafficking to areas of injury as well as to locations where primary immune responses are initiated (secondary lymphoid tissues such as lymph nodes, spleen, Peyer's patches, and tonsils). There are presently four classes of chemokine molecules (C, CC, CXC, and CX3C) that are named for the number and location of cysteine residues on the amino terminus of the protein. These molecules communicate with their target cells via G-protein coupled receptors that are pertussis toxin sensitive. Different chemokines act on different leukocyte populations, thereby modulating the influx of immune effector cells to the area in question based on the needs of the particular situation.

Chemokines are secreted proteins involved in immunoregulatory and inflammatory processes. The chemokines used in the present methods are shown in Table 1.

TABLE 1

Chemokines

| Gene Symbol | Gene Name | GenBank Acc. No: Nucleic Acid | GenBank Acc. No: Amino Acid |
|---|---|---|---|
| CCL2 | chemokine (C—C motif) ligand 2 | NM_002982.3 | NP_002973.1 |
| CCL3 | chemokine (C—C motif) ligand 3 | NM_002983.2 | NP_002974.1 |
| CCL4 | chemokine (C—C motif) ligand 4 | NM_002984.2 | NP_002975.1 |
| CCL5 | chemokine (C—C motif) ligand 5 | NM_002985.2 | NP_002976.2 |
| CCL8 | chemokine (C—C motif) ligand 8 | NM_005623.2 | NP_005614.2 |
| CCL18 | chemokine (C—C motif) ligand 18 (pulmonary and activation-regulated) | NM_002988.2 | NP_002979.1 |
| CCL19 | chemokine (C—C motif) ligand 19 | NM_006274.2 | NP_006265.1 |
| CCL21 | chemokine (C—C motif) ligand 21 | NM_002989.2 | NP_002980.1 |
| CXCL9 | chemokine (C—X—C motif) ligand 9 | NM_002416.1 | NP_002407.1 |
| CXCL10 | chemokine (C—X—C motif) ligand 10 | NM_001565.2 | NP_001556.2 |
| CXCL11 | chemokine (C—X—C motif) ligand 11 | NM_005409.4 | NP_005400.1 |
| CXCL13 | chemokine (C—X—C motif) ligand 13 | NM_006419.2 | NP_006410.1 |

In some embodiments, the chemokine is selected from within the classes C, CC, CXC, and CX3C, e.g., as shown in Table 2.

TABLE 2

Chemokines and their Receptors

| Name | Gene | Other name(s) | Receptor | Uniprot |
|---|---|---|---|---|
| CC chemokines ||||| 
| CCL1 | Scya1 | I-309, TCA-3 | CCR8 | |
| CCL2 | Soya2 | MCP-1 | CCR2, CCR2 | P13500 |
| CCL3 | Scya3 | MIP-1a | CCR1 | P10147 |
| CCL4 | Scya4 | MIP-1β | CCR1, CCR5 | P13236 |
| CCL5 | Scya5 | RANTES | CCR5 | P13501 |
| CCL6 | Soya6 | C10, MRP-2 | CCR1 | P27784 |
| CCL7 | Soya7 | MARC, MCP-3 | CCR2 | P80098 |
| CCL8 | Scya8 | MCP-2 | CCR1, CCR2B, CCR5 | P80075 |
| CCL9/CCL10 | Scya9 | MRP-2, CCF18, MIP-1 | CCR1 | P51670 |
| CCL11 | Scya11 | Eotaxin | CCR2, CCR3, CCR5 | P51671 |
| CCL12 | Scya12 | MCP-5 | | Q62401 |
| CCL13 | Soya13 | MCP-4, NCC-1, Ckβ10 | CCR2, CCR3, CCR5 | Q99616 |
| CCL14 | Scya14 | HCC-1, MCIF, Ckβ1, NCC-2, CCL | CCR1 | Q16627 |
| CCL15 | Scya15 | Leukotactin-1, MIP-5, HCC-2, NCC-3 | CCR1, CCR3 | Q16663 |
| CCL16 | Scya16 | LEC, NCC-4, LMC, Ckβ12 | CCR1, CCR2, CCR5, CCR8 | O15467 |
| CCL17 | Soya17 | TARC, dendrokine, ABCD-2 | CCR4 | Q92583 |
| CCL18 | Soya18 | PARC, DC-CK1, AMAC-1, Ckβ7, MIP-4 | | P55774 |
| CCL19 | Scya19 | ELC, Exodus-3, Ckβ11 | CCR7 | Q99731 |
| CCL20 | Scya20 | LARC, Exodus-1, Ckβ4 | CCR6 | P78556 |
| CCL21 | Soya21 | SLC, 6Ckine, Exodus-2, Ckβ9, TCA-4 | CCR7 | O00585 |
| CCL22 | Scya22 | MDC, DC/β-CK | CCR4 | O00626 |
| CCL23 | Scya23 | MPIF-1, Ckβ8, MIP-3, MPIF-1 | CCR1 | P55773 |
| CCL24 | Scya24 | Eotaxin-2, MPIF-2, Ckβ6 | CCR3 | O00175 |
| CCL25 | Scya25 | TECK, Ckβ15 | CCR9 | O15444 |
| CCL26 | Scya26 | Eotaxin-3, MIP-4a, IMAC, TSC-1 | CCR3 | Q9Y258 |
| CCL27 | Scya27 | CTACK, ILC, Eskine, PESKY, skinkine | CCR10 | Q9Y4X3 |
| CCL28 | Scya28 | MEC | CCR3, CCR10 | Q9NRJ3 |
| CXC chemokines |||||
| CXCL1 | Scyb1 | Gro-a, GRO1, NAP-3, KC | CXCR2 | P09341 |
| CXCL2 | Scyb2 | Gro-β, GRO2, MIP-2a | CXCR2 | P19875 |
| CXCL3 | Scyb3 | Gro-?, GRO3, MIP-2β | CXCR2 | P19876 |
| CXCL4 | Scyb4 | PF-4 | CXCR3B | P02776 |
| CXCL5 | Scyb5 | ENA-78 | CXCR2 | P42830 |
| CXCL6 | Scyb6 | GCP-2 | CXCR1, CXCR2 | P80162 |
| CXCL7 | Scyb7 | NAP-2, CTAPIII, β-Ta, PEP | | P02775 |
| CXCL8 | Soyb8 | IL-8, NAP-1, MDNCF, GCP-1 | CXCR1, CXCR2 | P10145 |
| CXCL9 | Scyb9 | MIG, ORG-10 | CXCR3 | Q07325 |
| CXCL10 | Scyb10 | IP-10, CRG-2 | CXCR3 | P02778 |
| CXCL11 | Scyb11 | I-TAC, β-R1, IP-9 | CXCR3 | O14625 |
| CXCL12 | Scyb12 | SDF-1, PBSF | CXCR4 | P48061 |
| CXCL13 | Scyb13 | BCA-1, BLC | CXCR5 | O43927 |
| CXCL14 | Scyb14 | BRAK, bolekine | | O95715 |
| CXCL15 | Scyb15 | Lungkine, WECHE | | Q9WVL7 |
| CXCL16 | Soyb16 | SRPSOX | | Q9H2A7 |
| CXCL17 | VCC-1 | DMC, VCC-1 | | Q6UXB2 |
| XCL1 | Scyc1 | Lymphotactin a, SCM-1a, ATAC | XCR1 | P47992 |
| XCL2 | Scyc2 | Lymphotactin β, SCM-1β | XCR1 | Q9UBD3 |
| CX3C chemokines |||||
| CX3CL1 | Scyd1 | Fractalkine, Neurotactin, ABCD-3 | CX3CR1 | P78423 |

Microparticles

In some embodiments, the chemokines are encapsulated in a microparticle, such as a lipid-enveloped mesoporous microparticle.

Suitable mesoporous materials include organic and inorganic materials. More specifically, suitable mesoporous materials include mesoporous silicon, mesoporous silica, mesoporous silicate, mesoporous starch, mesoporous carbon, mesoporous alumina, mesoporous titania, and mesoporous carbonate.

Mesoporous materials contain pores having a diameter in the range of 2 to 50 nm and microparticles are particles of about 1 to 1000 μm in diameter. Particle size distribution measurements, including the mean particle size (d50/μm) of the particles can be measured using a Malvern Particle Size Analyzer, Model Mastersizer, from Malvern Instruments. Mesopore diameters can be measured by very high resolution electron microscopy. This technique and other suitable techniques which include gas-adsorption-desorption analysis, small angle x-ray scattering, NMR spectroscopy or thermoporometry, are described by R. Herino in "Properties of Porous Silicon", chapter 2.2, 1997.

Methods for making microparticles are well known in the art. These include chemical or gas phase synthesis methods or electrochemical etching or comminution. As used herein, and unless otherwise stated, the term "silicon" refers to solid elemental silicon. For the avoidance of doubt, and unless otherwise stated, it does not include silicon-containing chemical compounds such as silica, silicates or silicones, although it may be used in combination with these materials.

The purity of the silicon may depend to some extent on the final application of the mesoporous silicon. For example, the silicon may be about 95 to 99.99999% pure, for example about 96 to 99.9% pure. The physical forms of silicon which are suitable for use according to the present invention may be chosen from or comprise one or more of amorphous silicon, single crystal silicon and polycrystalline silicon (including nanocrystalline silicon, the grain size of which is typically taken to be 1 to 100 nm) and including combinations thereof. Any of the above-mentioned types of silicon may be porosified to form mesoporous silicon.

Suitable other mesoporous materials include: mesoporous silicates (or bioactive glasses); mesoporous carbonates; mesoporous silica gels; mesoporous starch derivatives; mesoporous alumina; mesoporous carbon materials; and mesoporous titania.

The ingredient to be loaded with the mesoporous material may be dissolved or suspended in a suitable solvent, and mesoporous particles may be incubated in the resulting solution for a suitable period of time. Both aqueous and non-aqueous slips have been produced from ground silicon powder. The removal of solvent will result in the ingredient penetrating into the pores of the mesoporous material by capillary action, and, following solvent removal, the ingredient will be present in the pores. Preferred solvents, at least for use in connection with mesoporous silicon, include water, ethanol, and isopropyl alcohol, GRAS solvents and volatile liquids amenable to freeze drying.

Typically, the one or more ingredients are present in the range, in relation to the loaded mesoporous microparticulate material, of 0.01 to 90 wt %, for example 1 to 40 wt %, for example 20 to 50 wt % (optionally, in combination with about 70% porosity) and for example 2 to 10 wt %.

Higher levels of loading of the loaded ingredient based on the loaded weight of the mesoporous material may be achieved by performing the impregnation at an elevated temperature. For example, loading may be carried out at a temperature which is at or above the melting point of the ingredient to be loaded. Quantification of gross loading may conveniently be achieved by a number of known analytical methods, including gravimetric, EDX (energy-dispersive analysis by x-rays), Fourier transform infra-red (FTIR), Raman spectroscopy, UV spectrophotometry, titrimetric analysis, HPLC or mass spectrometry. If required, quantification of the uniformity of loading may be achieved by techniques that are capable of spatial resolution such as cross-sectional EDX, Auger depth profiling, micro-Raman and micro-FTIR. The loading levels can be determined by dividing the volume of the ingredient taken up during loading (equivalent to the mass of the ingredient taken up divided by its density) by the void volume of the mesoporous material (e.g. silicon) prior to loading multiplied by one hundred.

The capping layer serves to encapsulate the mesoporous microparticulate material. In encapsulating the mesoporous material, the openings to the pores are sealed. Typically, the whole of the particle, or substantially all of the particle, is coated with the capping layer. The capping layer at least seals the openings to the pores at the surface of the mesoporous material, thus ensuring that the at least one loaded ingredient is retained. The thickness of the capping layer may be about 0.1 to 50 μm in thickness, for example about 1 to 10 μm, for example about 1 to 5 μm. The capping layer may provide retention of an ingredient over a period of a few months to many months, for example up to about 5 years, followed by triggered release through site specific degradation which may occur in or on the animal body. The capping layer may be an organic or an inorganic capping layer. The thickness of the capping layer can be measured by mechanically fracturing a number of the capped particles and examining their cross-sectional images in a high resolution scanning electron microscope, equipped with energy dispersive x-ray analysis (EDX analysis) of chemical composition.

The capping layer or layers is in some cases a lipid. Suitable examples of lipids include fats, hardened oils, paraffin, stearic acid, wax, diglycerides, monoglycerides.

Suitable methods for capping the mesoporous material include: spray drying, fluidized bed coating, pan coating, modified microemulsion techniques, melt extrusion, spray chilling, complex coacervation, vapour deposition, solution precipitation, emulsification, supercritical fluid techniques, physical sputtering, laser ablation, very low temperature sintering and thermal evaporation.

Stromal Cells

In some embodiments, the chemokines are released from lymph node-derived stromal cells. In some cases, the cells are from monoclonal cell line 1.F3 stromal cells.

Chitosan-Based Hydrogels

The disclosed microparticles or stroma cells can be embedded in a hydrogel, such as a thermosensitive chitosan-based hydrogel.

Various natural and synthetic thermosensitive polymers are used including natural polymers, such as cellulose derivatives and chitosan, as well as synthetic polymers, such as poly (Msopropylacrylamide) and Poloxamer.

Chitosan and its derivatives represent a particularly attractive group of biocompatible and degradable polymers. Chitosan is biocompatible, non-toxic, and non-immunogenic, allowing its use in the medical, pharmaceutical, cosmetic and tissue construction fields. Moreover, chitosan is cleaved by certain specific enzymes, e.g. lysozyme, and can therefore be considered as bioerodable and biodegradable.

The preparation of thermosensitive, neutral solutions based on chitosan/polyol salt combinations has been described. These formulations possess a physiological pH and can be held liquid below room temperature in order to encapsulate living cells and therapeutic proteins; they form monolithic gels at body temperature, without any chemical modification or cross-linking. The addition of polyol salts bearing a single anionic head results in the formation of a gel due to synergistic forces favorable to gel formation, such as hydrogen bonding, electrostatic interactions and hydrophobic interactions. When injected in vivo the liquid formulation turns into gel implants in situ. The system has been used as a container-reservoir for delivery of biologically active growth factors in vivo as well as an encapsulating matrix for living chondrocytes for tissue engineering applications.

An advanced clinical product of such chitosan hydrogels is a hydrogel produced by BioSyntech, described in WO 99/07416. The thermosensitive chitosan hydrogel of Bio-Syntech is prepared by neutralizing a commercial chitosan, having a degree of deacetylation of about 80-90%, with mono-phosphate dibasic salts of polyols, particularly β-glycerophosphate. Addition of β-glycerophosphate to chitosan enables the pH to be increased up to about 7 without chitosan precipitation, and to form a hydrogel at that pH, at physiological temperature.

The term "chitosan" will be understood by those skilled in the art to include all derivatives of chitin, or poly-N-aceryl-D-glucosamine, including all polyglucosamine and oligomers of glucosamine materials of different molecular weights, in which the greater proportion of the N-acetyl groups have been removed through hydrolysis, and all salts thereof. Synthetically produced beta-1,4-poly-D-glucosamines and derivatives thereof of equivalent structure to chitosan may also be used according to this invention.

Salts with various organic and inorganic acids are suitable. Such suitable salts include, but are not limited to, lactate, citrate, glutamate, nitrate, phosphate, acetate, malate, propionate, ascorbate, formate and the like. Preferred salts are chitosan chloride And chitosan lactate.

Chitosan derivatives are also suitable for use in this invention. Suitable chitosan derivatives include, without limitation, esters, ethers or other derivatives formed by bonding acyl and/or alkyl groups with the hydroxyl groups, but not the amino groups of chitosan. Examples include O-alkyl ethers of chitosan and O-acyl esters of chitosan. Modified chitosans, such as those conjugated to polyethylene glycol may be used in the present invention.

The chitosan or chitosan derivative or salt used preferably has a molecular weight of 4,000 Dalton or more, preferably in the range 25,000 to 2,000,000 Dalton, and most preferably about 50,000 to 300,000 Dalton.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Tertiary lymphoid structures (TLSs) have been identified in the parenchyma and/or in the peripheral margins of human solid tumors. Uncovering the functional nature of these structures is the subject of much intensive investigation. Studies have shown a direct correlation of the presence of human tumor-localized TLS and better patient outcome (e.g., increase in overall survival) in certain solid tumor histologies, but not all. A tumor-derived immune gene-expression signature, encoding 12 distinct chemokines, was identified which could reliably identify the presence of TLSs, of different degrees, in various human solid tumors. There is a need to understand the influence of TLSs on the tumor microenvironment and leveraging this understanding to both manipulate the antitumor immune response and potentially enhance immunotherapy applications. Moreover, as not all human solid tumors show the presence of these lymphoid structures, bioengineering approaches are needed to design and build "designer" TLSs to address, and potentially overcome, an unmet medical need in cancer patients whose tumors lack such lymphoid structures.

Despite the clinical success with antibodies against CTLA-4 and PD-1, cytokines (e.g., high-dose interleukin-2), as well as the adoptive transfer of tumor-infiltrating lymphocytes (TILs), many patients treated with those agents fail to respond in a clinically meaningful manner. Employing Moffitt Cancer Center's revolutionary Total Cancer Care (TCC) bio-repository (>38,000 tumors), genomic database (>16,000 tumor gene-expression arrays; ~ 5,000 tumor whole genome, whole exome, and targeted gene sequences), and longitudinal clinical database (on>100,000 TCC consented patients), a unique 12-chemokine (CCL2, CCL3, CCL4, CCL5, CCL8, CCL18, CCL19, CCL21, CXCL9, CXCL10, CXCL11, and CXCL13) gene-expression signature (GES) was identified from a metagene grouping with overwhelming enrichment for immune-related and inflammation-related genes. The GES was interrogated on 14,492 distinct solid tumors of 24 distinct tissue types (primaries and metastases) in TCC (modified Affy chip) and confirmed on another set of >7,000 samples in the TCGA database (RNASeq) and showed distribution across different histologies, including breast, lung, melanoma, and colorectal cancers of differing degrees (Coppola D, et al. J Clin Oncol (2008) 26:4369-70; Coppola D, et al. Am J Pathol (2011) 179:37-45; Messina J L, et al. Sci Rep (2012) 2:765; Mihm MC, et al. Cancer Immunol Res (2015) 3:827-35). This 12-chemokine GES could accurately predict the degree and type of lymphoid infiltrate, organized remarkably as tumor-localized, tertiary lymphoid structures (TL-TLSs) that comprise—by immunohistochemistry staining—prominent B cell follicles, T cell marginal zones, and associated follicular dendritic cells (DCs) but few, if any, T regulatory cells (Coppola D, et al. Am J Pathol (2011) 179:37-45; Messina J L, et al. Sci Rep (2012) 2:765; Mihm MC, et al. Cancer Immunol Res (2015) 3:827-35). TL-TLSs appear to exhibit similar structural and cellular characteristics of peripheral lymph nodes and presumably arise in the tumor microenvironment in response to chronic inflammation (Hiraoka N, et al. Front Immunol (2016) 7:244; Sautes-Fridman C, et al. Front Immunol (2016) 7:407).

Of importance, there was a highly significant and consistent association between a marked increase in overall patient survival, the value of the mean score of the GES, and the presence of TL-TLSs in stage IV (non-locoregional) melanoma, colorectal cancer, and, most recently, in stage IV bladder cancer, non-small cell lung cancer, and certain types of breast cancer, especially in basal and HER2+patients. Moreover, solid tumor radiosensitivity across a spectrum of histologies is associated with immune activation as measured by the GES1 (Prabhakaran S, et al. Breast Cancer Res (2017) 19:71). It remains unclear whether TLSs are either only a consequence of an immune response per se or sites of an active immune reaction against the local tissue components. With respect to the latter, TLSs are associated with longer survival of cancer patients, aggravation of graft rejection, and presence of auto-immune inflammatory disease (Dieu-Nosjean MC, et al. Trends Immunol (2014) 35:571-80). TLSs have also been observed as a consequence of immunization with certain vaccines. As examples, intramuscular vaccination targeting HPV16 in patients with cervical intraepithelial neoplasia induced cervical tissue immune infiltrates, including organized TLSs (Maldonado L, et al. Sci Transl Med (2014) 6: 221ra13). In a pancreatic ductal adenocarcinoma clinical trial, an irradiated, allogeneic granulocyte-macrophage colony-stimulating factor-secreting pancreatic tumor cell vaccine converted a "nonimmunogenic" neoplasm into an "immunogenic" one by inducing formation of TLSs (Lutz ER, et al. Cancer Immunol Res (2014) 2:616-31). Gene-expression analysis of the vaccine-induced TLSs showed a suppressed Treg pathway and an enhanced Th17 pathway, which was associated with improved patient survival and elicitation of mesothelin-specific T-cell responses. In another study in mice with deficiency of secondary lymphoid organs, infection of influenza virus could stimulate neogenesis of lung TLSs that produced an efficient protective immune response (Moyron-Quiroz JE, et al. Immunity (2006) 25:643-54). Collectively, these studies argue indirectly in favor of an active participatory role of TLSs in effective immune responses. Therefore, local induction of TLSs in the tumor microenvironment could be a promising therapeutic strategy to exploit against cancer.

The 12-chemokine GES has now provided the actual gene leads for potentially constructing bioengineered "designer lymph nodes." The novel platform is based on the improvement, manipulation, and stimulation of the host's own immune system. Specialized antigen-presenting DC were designed, produced from the host's blood or bone marrow, which is both antigen(s) loaded and genetically manipulated to express highly selected chemokine genes combined with biomaterial scaffolds prior to administration into cancer-bearing hosts (Weber JS, et al. Nat Biotechnol (2015) 33:44-5). This gene-modified cell-scaffold platform "design builds" a functioning "lymph node" on its own at any administration site that then produces a preplanned immunologic response against cancer cells locally and then throughout the host's body. The technology includes the option of providing gene-modified cell-scaffold platforms at multiple, independent sites to create multiple, independent "lymph nodes" of the same function and specificity concurrently. The administrations can also be staggered to create additional new structures over time. Moreover, by administering pools of different gene-modified cell-scaffold platforms, these structures can act independently of each other and create distinct functioning "lymph nodes" in the same host. Utilized by the host, these "designer lymph nodes" can provide an enhanced, unified, or diversified immune system to fight cancer.

Tertiary lymphoid structures have been described in animal models. Previous studies on gene knockout mice have identified the role of lymphotoxin (LT) in development of lymphoid organs (Weber JS, et al. Annu Rev Immunol (1999) 17:399-433). LTa-deficient mice, which lack the soluble LTa3 homotrimer as well as the membrane LT1ß2 heterotrimer, show absence of Peyer's patches and all peripheral lymph nodes (Alexopoulou L, et al. J Exp Med (1998) 188:745-54; Liepinsh D J, et al. Mol Cell Biol (2006) 26:4214-25). LTB-deficient mice also displayed similar defect with residual mesenteric and cervical lymph nodes (Alimzhanov MB, et al. Proc Natl Acad Sci USA (1997) 94:9302-7). Consistently, transgenic mouse models that ectopically express LTa or LTB demonstrate formation of TLSs in non-lymphoid tissues. For instance, restricted expression of LTa or LTa/LTB in kidney and pancreas induced organized infiltrates in these sites that show similar cellular composition to lymphoid organs. T cells, B cells, plasma cells, antigen-presenting cells, and features of high-endothelial venules (HEV) were observed in the infiltrates (Drayton DL, et al. J Exp Med (2003) 197:1153-63; Kratz A, et al. J Exp Med (1996) 183:1461-72). These studies suggest that the formation of TLSs involves the same signaling pathways in development of the secondary lymphoid organs.

In addition to the LT pathway, several transgenic mouse models with overexpression of chemokines that are important for recruiting immune cells displayed TLSs. In a transgenic mouse model with pancreatic islet-specific expression of CCL21, spontaneous development and organization of lymphoid tissues composed of T cells, DC, B cells, HEV, and stroma reticulum was observed (Fan L, et al. J Immunol (2000) 164:3955; Chen SC, et al. J Immunol (2002) 168: 1001-8). Similarly, constitutive expression of CCL21 in thyroid resulted in significant lymphocytic infiltrates, which are topologically arranged into B and T cell areas (Martin AP, et al. J Immunol (2004) 173:4791-8). In addition to CCL21, ectopic expression of another three important homeostatic chemokines CCL19, CXCL12, and CXCL13 in pancreatic islet led to formation of TLSs with different size, cellular composition, and organization (Luther SA, et al. J Immunol (2002) 169:424-33; Luther S A, et al. Immunity (2000) 12:471-81). Moreover, transplantable and functional "artificial" TLSs could be constructed from slow-releasing gels containing different lymphogenesis-related chemokines and ligands (Kobayashi Y, et al. Front Immunol (2016) 7:316). Therefore, the formation of TLSs could be achieved by chemokine-mediated accumulation of lymphocytes.

Sound preclinical models of TLS formation are being developed in which multiple elements are being interrogated for the capacity to recruit and design an antitumor immune system. The inclusion of lymph node-derived primary cellular components, which normally provide chemotactic and homeostatic cues in conventional lymph nodes (Barone F, et al. Front Immunol (2016) 7:477), are being genetically modified to express selected chemotactic and lymphoid neogenesis-related genes to enhance TLS formation. Inclusion of activated DCs in a stromal cell-induced TLS model could markedly enhance the efficiency and organization of TLS formation (Suematsu S, et al. Nat Biotechnol (2004) 22:1539-45). The contributions of DCs to TLS induction have been reviewed elsewhere (Kobayashi Y, et al. Trends Immunol (2010) 31:422-8). In this regard, CD11c+DCs were necessary for maintenance of inducible bronchus-associated lymphoid tissues. Additionally, retinoic acid production by DCs from gut-associated lymphoid organs was involved in the imprinting of gut-homing receptors on activated T cells. Various modified cell lines are being combined with tumor antigen-pulsed DCs and then incorporated in biocompatible scaffold materials and administered to tumor-bearing mice as injectable or implantable matrices. These matrices should serve as model systems to better understand the factors governing the formation and/or maintenance of TLSs and also to identify and classify tumor-specific, therapeutic TIL. Additionally, these matrix-based systems may function as a therapeutic platform by delivering, stimulating, and expanding transplanted lymphocytes and/or modified DCs.

Scaffolds are typically three-dimensional microporous structures designed to enable ex vivo cell encapsulation and/or in vivo cell infiltration while providing mechanical support, cell adhesion, and a sustained supply of biological cues to promote cell migration and interactions (Malafaya PB, et al. Adv Drug Deliv Rev (2007) 59:207-33; Irvine D J, et al. Semin Immunol (2008) 20:137-46). The scaffolds must be biocompatibile and should maintain a robust state for adequate time to allow the development of a new tissue, while eventually undergoing degradation and be replaced by the new tissue. Based on the origin of materials, scaffolds can be classified into synthetic or natural polymeric systems (Irvine DJ, et al. Semin Immunol (2008) 20:137-46). Optical means were developed to track the fate of implanted materials (Artzi N, et al. Nat Mater (2011) 10:704-9) and embedded cells fate (Unterman S, et al. Adv Healthc Mater (2015) 4:2220-8) non-invasively over time. This enables us to study cell: material interactions in vivo and to rationally modify the materials, as needed, to attain the desired preclinical outcomes.

Synthetic polymers can be readily tailored and modified to provide excellent mechanical and chemical properties; however, they typically lack essential biological elements that are required to induce necessary cell responses. For example, poly(lactic acid), poly(glycolic acid), and poly (caprolactone) are the most widely used synthetic biodegradable polymers, but their hydrophobic nature limits their application in tissue engineering due to the insufficient water absorption, cell adhesion, and interactions. In contrast, hydrophilic synthetic polymers such as poly(ethylene glycol) (PEG) and poly(ethylene oxide) possess excellent solubility in a wide range of solvents. However, they are not biologically degradable; therefore, they can only be used as permanent implants or as low-molecular weight blocks in combination with other components to enable elimination from the body (Place ES, et al. Chem Soc Rev (2009) 38:1139-51).

Natural polymers are particularly attractive candidates for tissue-engineering applications, as they offer excellent biocompatibility. Unlike synthetic polymers, they can be biologically degraded into components, which are non-inflammatory or non-toxic. The reactive sites available in most of the natural polymers allow ligand conjugation, cross-linking, and other modifications to tune their properties for specific applications (Dang J M, et al. Adv Drug Deliv Rev (2006) 58:487-99). Protein-based natural polymers such as collagen and gelatin have the potential to control the cellular migration, proliferation, and organization during new tissue development, as they possess many features of extracellular matrix. However, they often suffer from batch-to-batch variations due to the difficulties associated with the purification processes. Polysaccharides (alginate, chitosan, starch, and hyaluronic acid derivatives) are another promising class of natural and biocompatible polymers. Chitosan in particular is an important example with an established safety profile in humans (Read RC, et al. Vaccine (2005) 23:4367-74; McNeela E A, et al. Vaccine (2004) 22:909-14).

In addition, a diverse collection of hybrid scaffolds using different combinations of synthetic and natural polymers has been developed for specific tissue-engineering applications. As examples, a polyurethane scaffold containing type I collagen and matrigel was used to create 3D lymph node T zone stromal models (Tomei AA, et al. J Immunol (2009) 183:4273-83). A different hybrid scaffold approach incorporating a collagen matrix into PEG hydrogel was used by Stachowiak and Irvine to improve the migration of loaded T cells and DCs within the framework (Stachowiak AN, et al. J Biomed Mater Res A (2008) 85:815-28). When needed, scaffolds can be doped with microparticles or nanoparticles for controlled release of soluble factors in addition to serving as a scaffold for cells. Such measures can provide sustained environmental cues to augment antigen-presenting DCs or lymphocyte longevity, maturation, and activation. Hence, synthetic materials can be modified to include biological cues and harbor sites for cells to serve as engineered scaffolds, which can be manufactured in a reproducible manner and with controlled properties. Hydrogels, in particular, can provide a controlled cell microenvironment for immune cells that enable the recruitment, expansion, and activation of immune cells ex vivo and in vivo (Singh A, et al. Adv Mater (2014) 26:6530-41). The choice of materials is dictated by the end use, including biocompatibility, immunogenicity, site of implantation, types of stimuli, and release kinetics. Hydrogels have been utilized in both active and passive immunotherapies. They can be used to deliver antigens, chemokines, and other factors to DCs, to induce T cell stimulation and B cell-mediated antibody responses, or they can allow for efficient encapsulation of immunomodulatory molecules as well as immune cells. Immune cells such as DCs can be activated ex vivo in hydrogels prior to their implantation or in vivo by immobilizing stimuli within the gels that would recruit and activate the cells inside the gels, as bioreactors. Localized administration of the immunomodulatory hydrogels next to the tumor site offers higher bioavailability and controlled release of embedded molecules or of factors from embedded/recruited cells, over time. In particular, injectable hydrogel-based adhesive scaffolds that can adhere to the surface of a tumor have been exploited to locally release molecules of interest to combat cancer (Gilam A, et al. Nat Commun (2016) 77:12868; Conde J, et al. Nat Mater (2016) 15:1128-38; Conde J, et al. Nat Mater (2016) 15:353-63; Conde J, et al. Proc Natl Acad Sci USA (2015) 112:1278-87).

Example 2

Methods

Recombinant mouse CCL19, CCL21, CXCL13, and lymphotoxin-alpha2/beta1 were encapsulated in lipid-enveloped mesoporous microparticles and embedded in a thermosensitive chitosan-based hydrogel solution. The resulting mixture was injected subcutaneously into C57BL/6 mice. At week 1-4 post injection, hydrogels and/or newly formed surrounding tissue were dissected from mice. Single-cell suspensions were prepared by mechanical dissociation and enzymatic digestion, and analyzed by flow cytometry to determine the infiltration of different immune cell subsets. The second approach included the use of a lymph node-derived stromal monoclonal cell line embedded in chitosan hydrogel.

Results

Figure 1B:
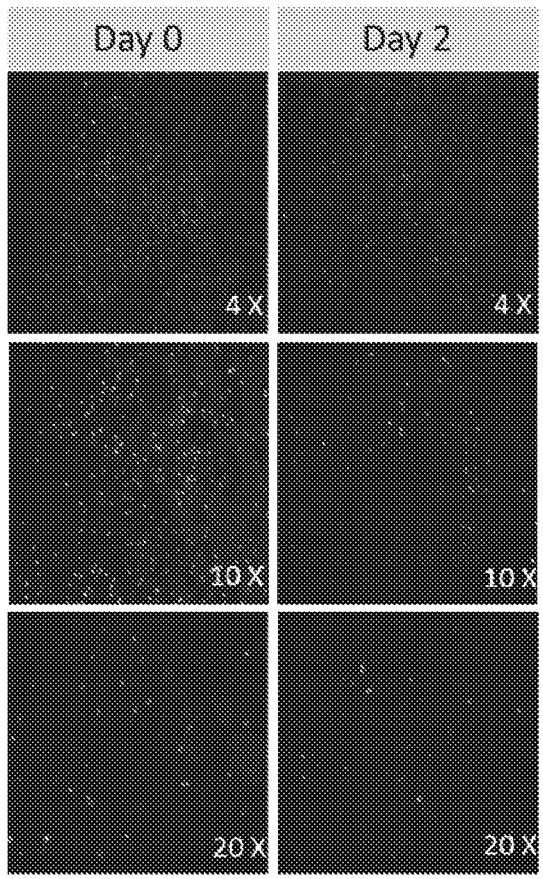
Figure 1B:
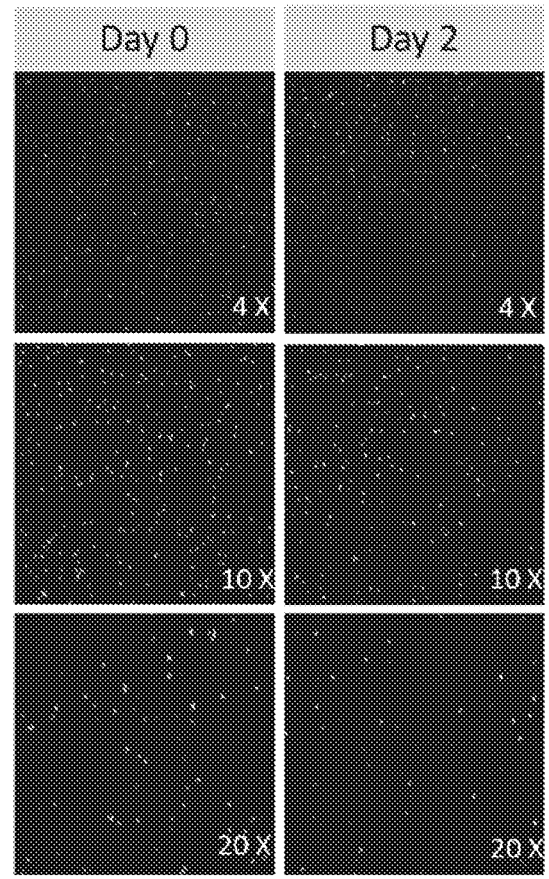
Figure 1C:
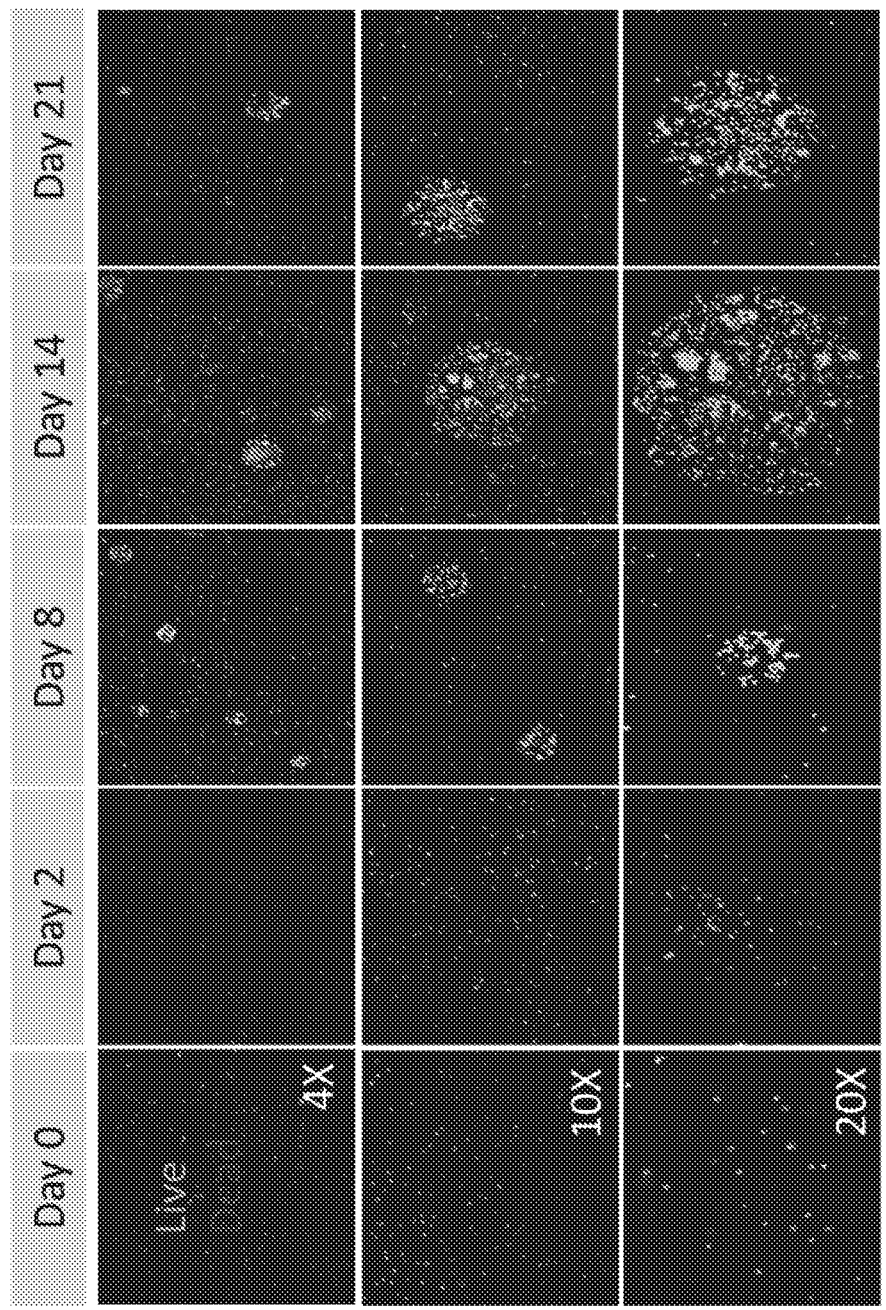
Figure 2A:
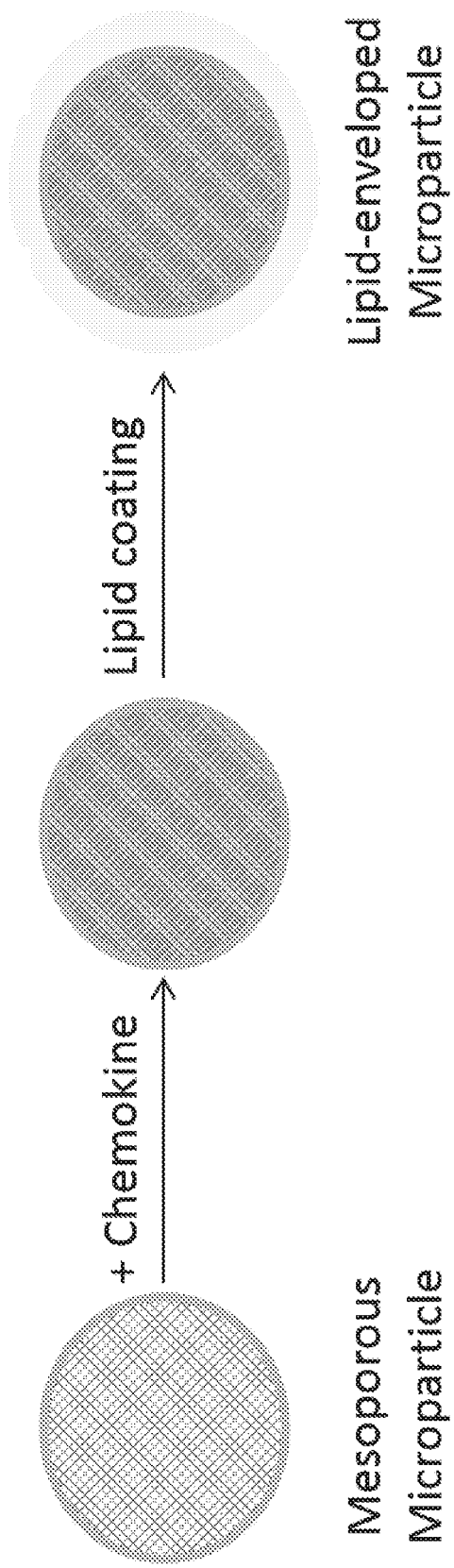
FIGS. 2A to 2D show characterization of lipid-enveloped microparticles (MPs) encapsulated with chemokines.
Figure 2B:
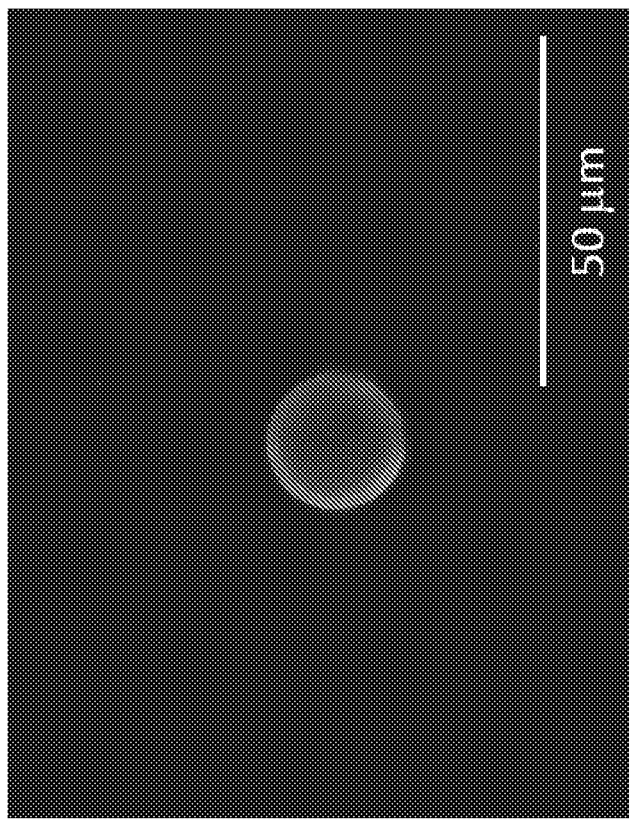
Figure 2B:
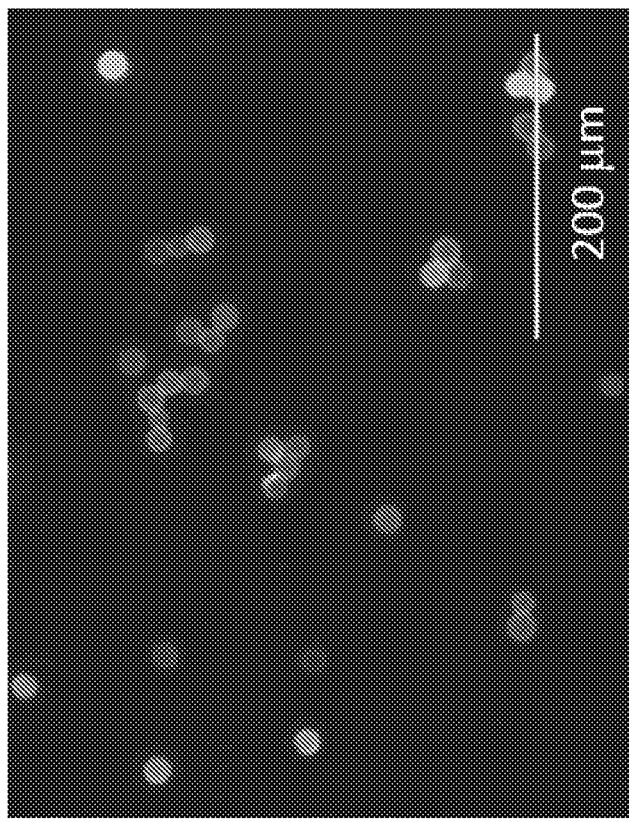
Figure 2C:
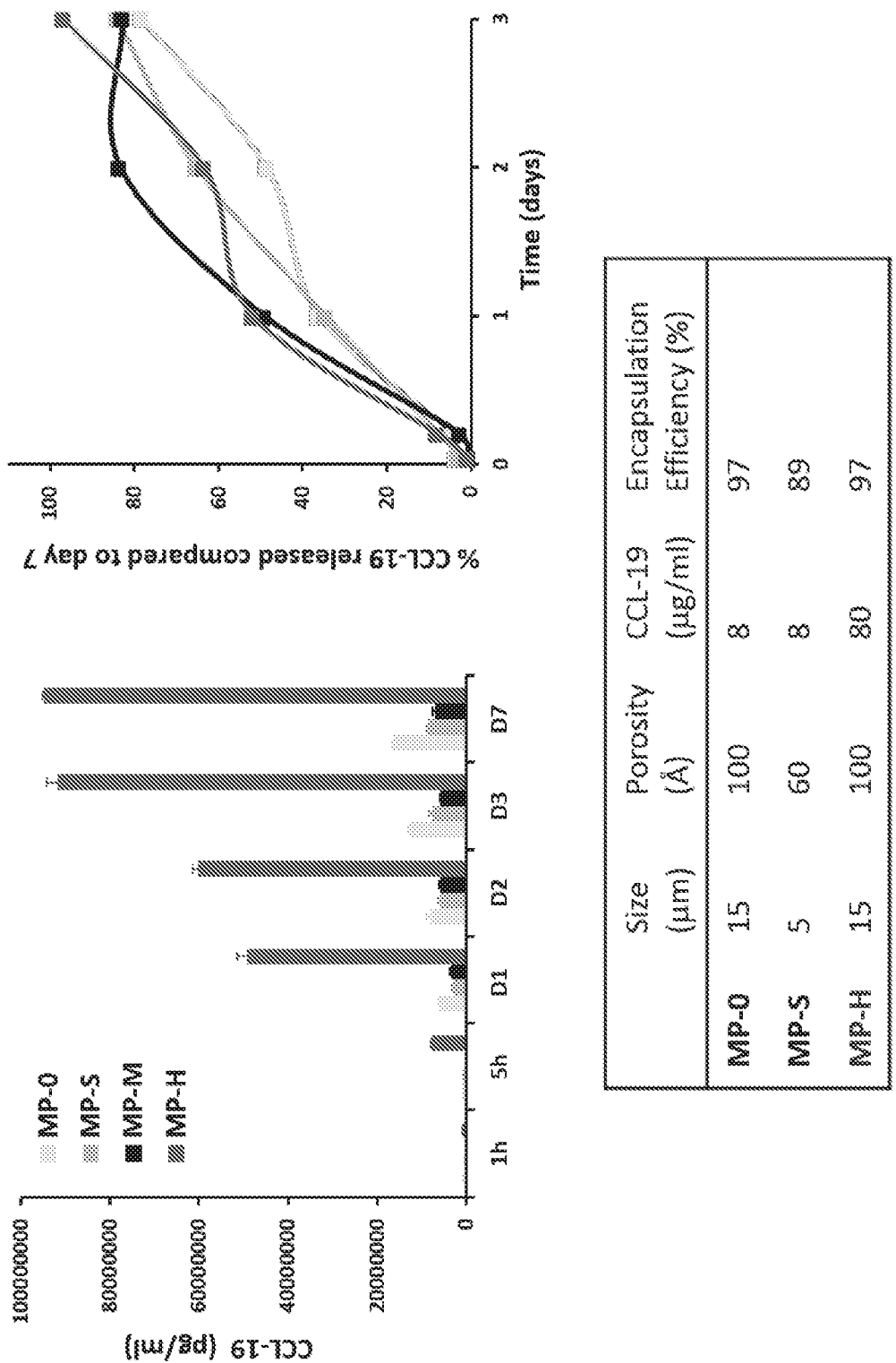
Figure 2D:
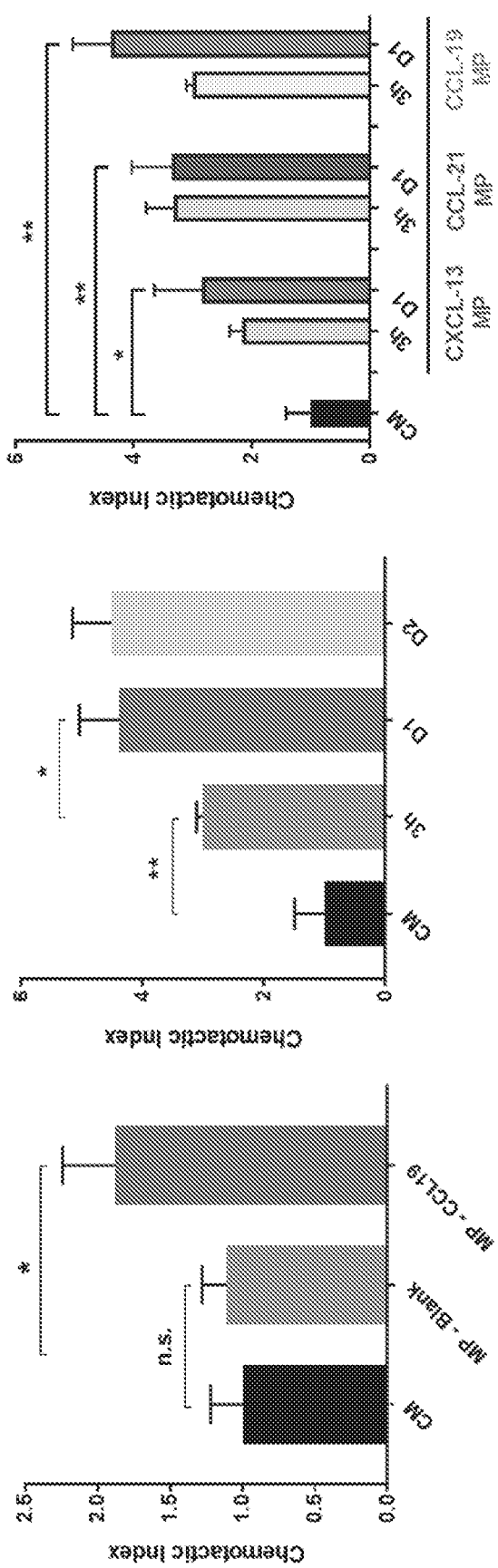
Figure 3A:
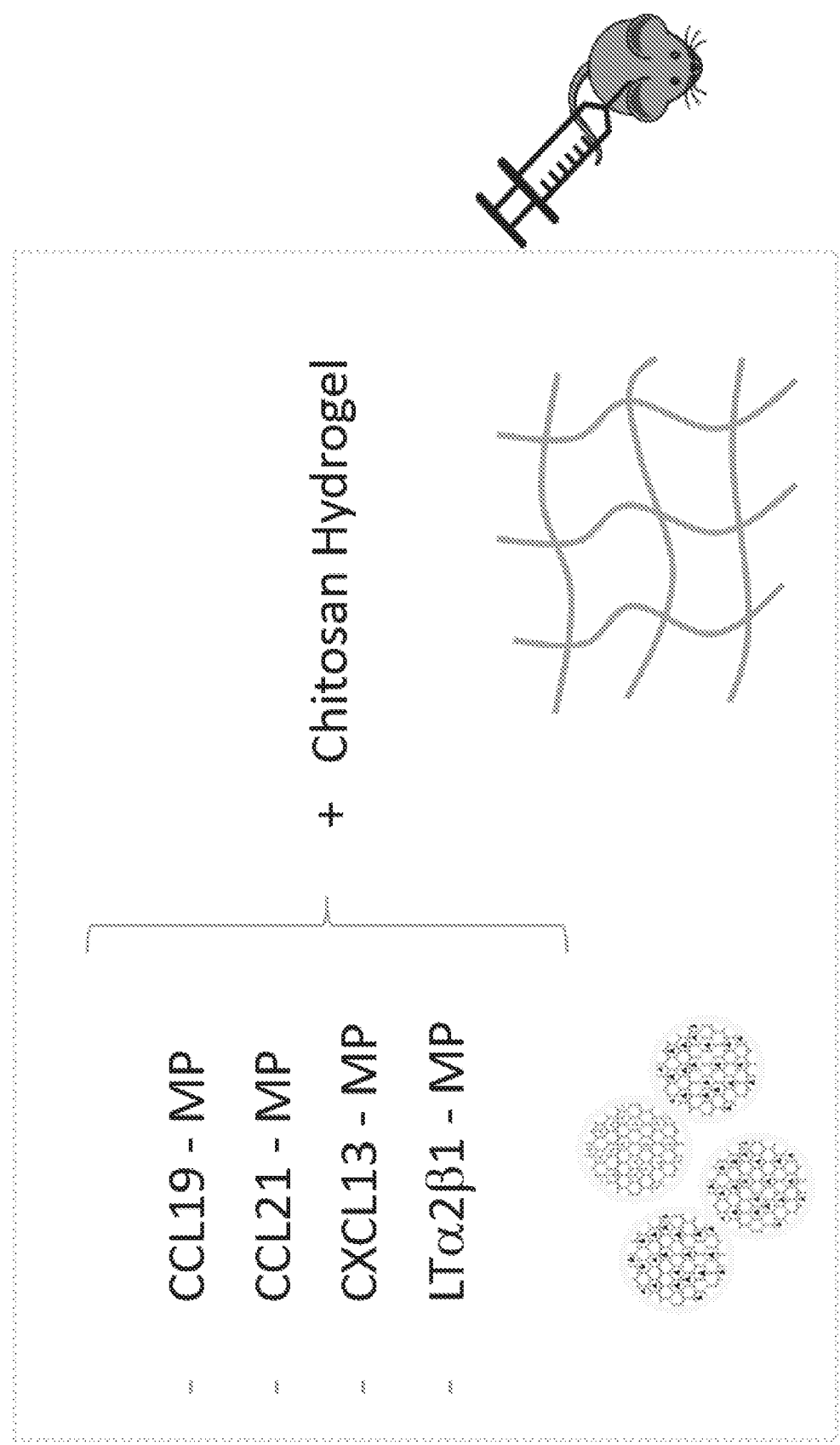
FIGS. 3A to 3E show bioengineering TLS using chemokine releasing MPs embedded in chitosan hydrogel.
Figure 3B:
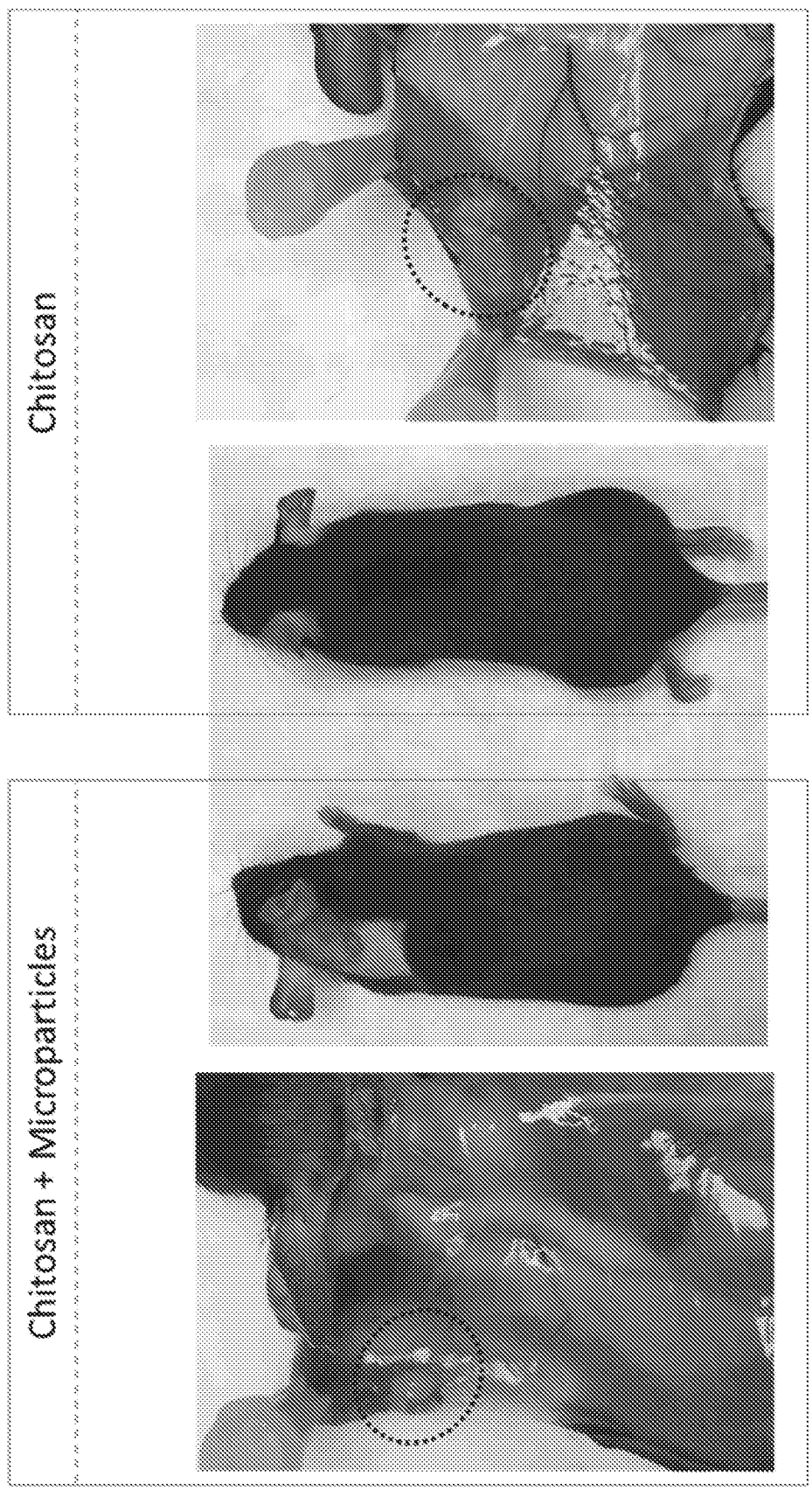
Figure 3C:
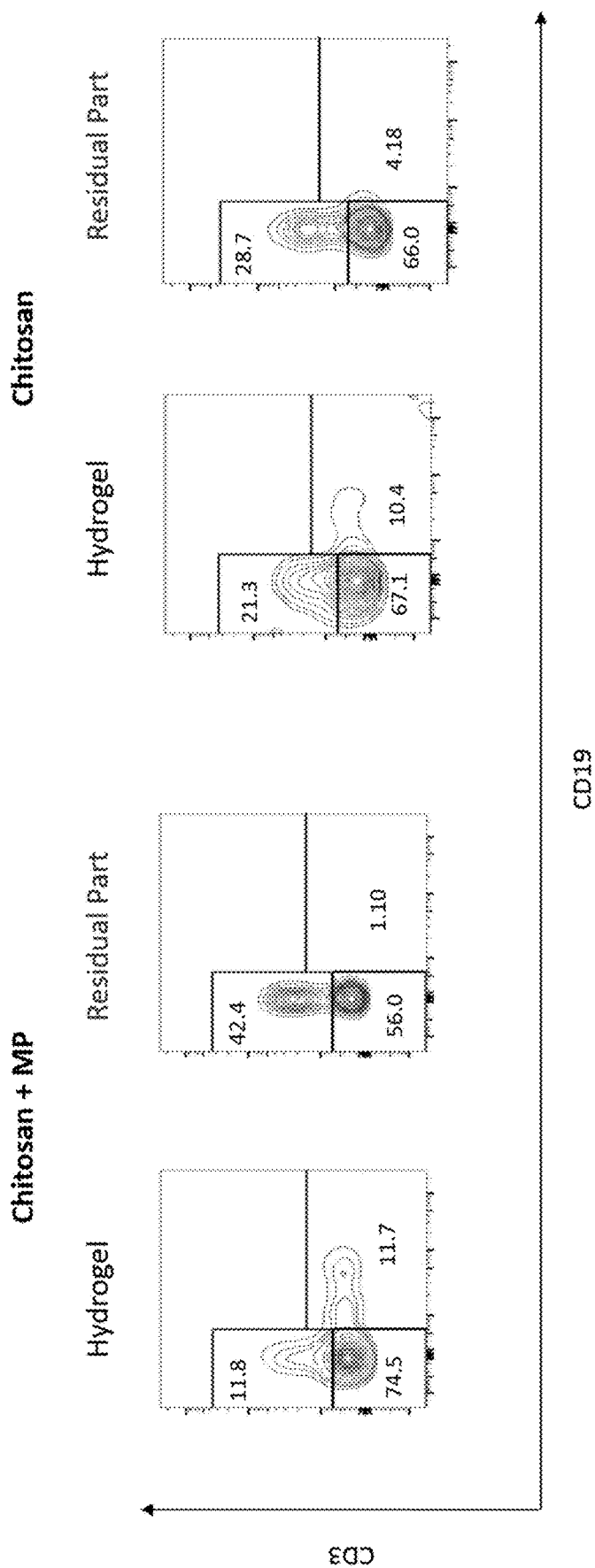
Figure 3D:
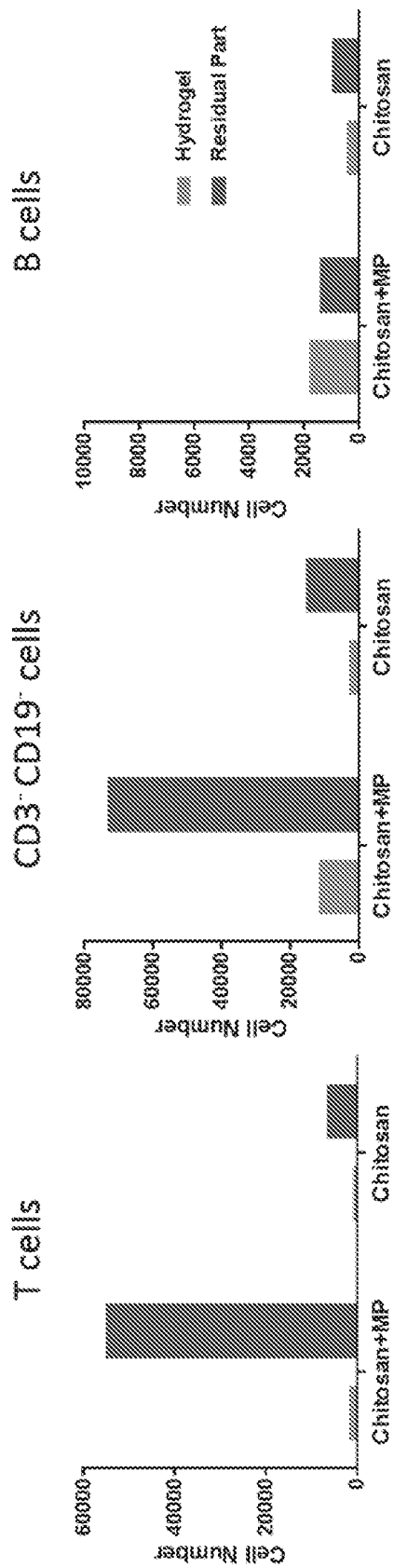
Figure 3E:
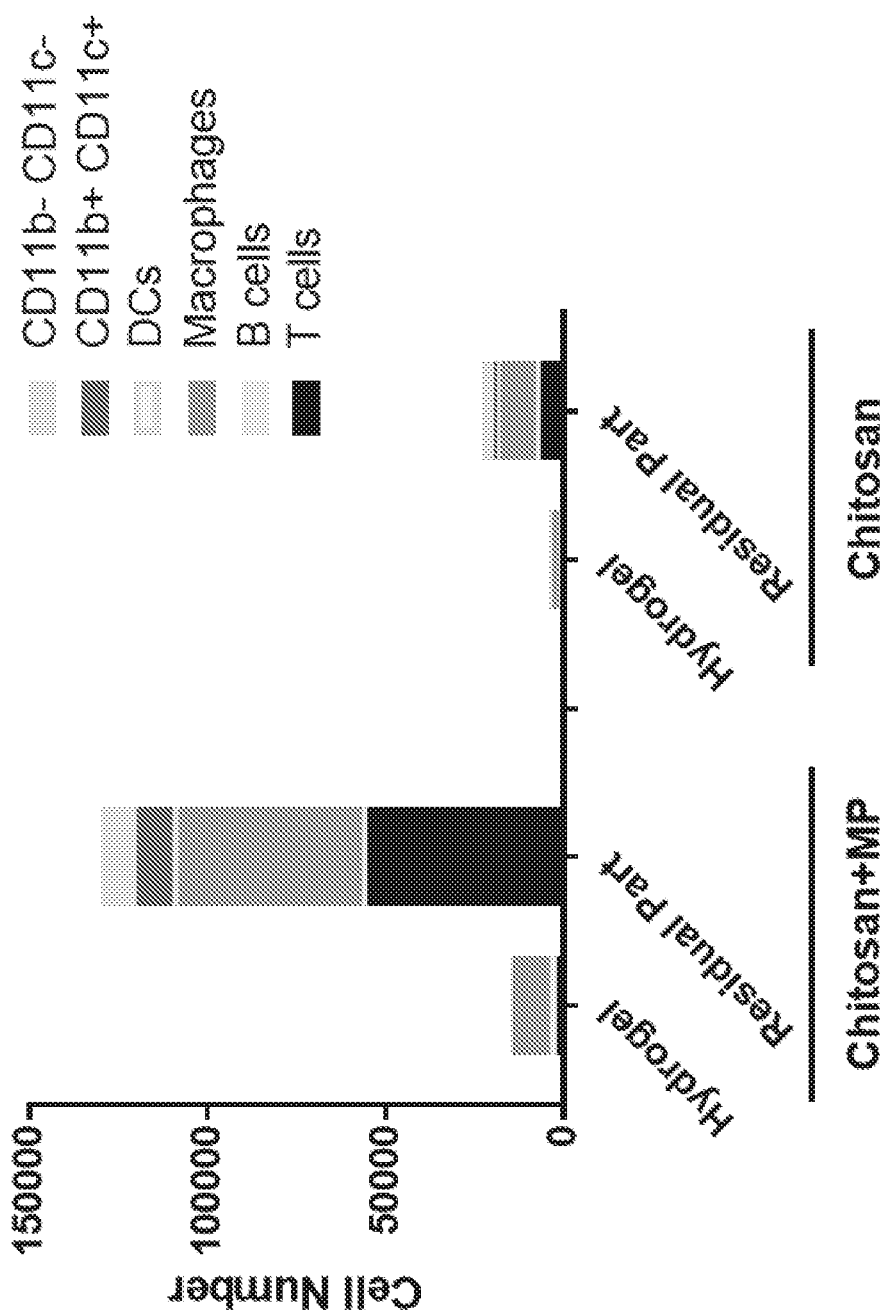
Figure 4A:
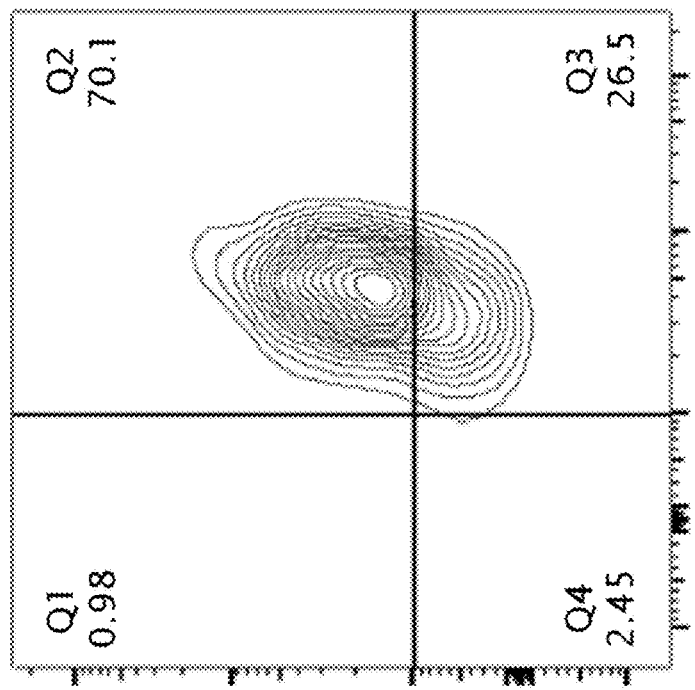
FIGS. 4A to 4D show bioengineering TLS using stromal cells embedded in chitosan hydrogel.
Figure 4A:
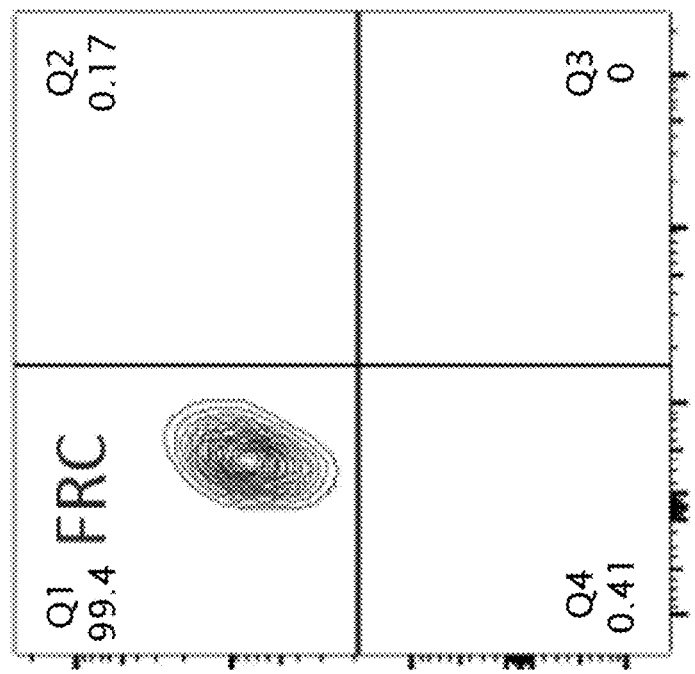
Figure 4B:
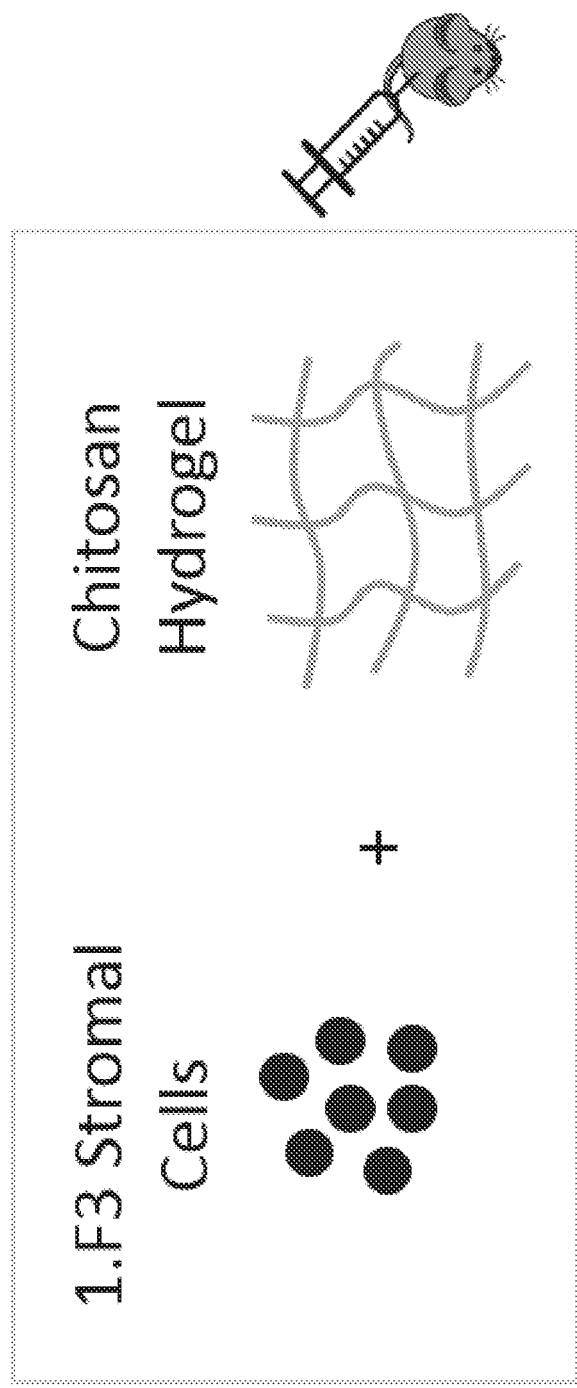
Figure 4C:
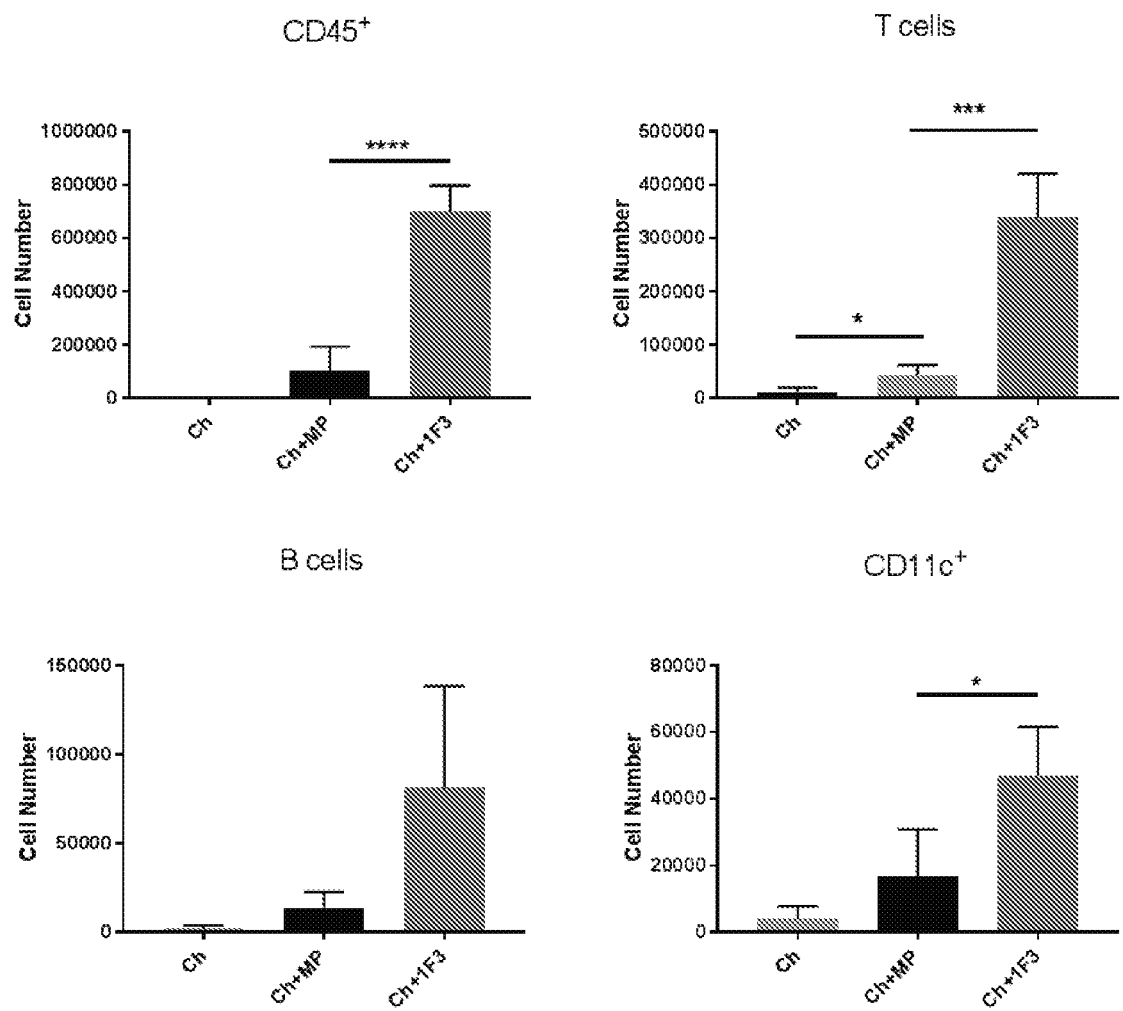
Figure 4D:
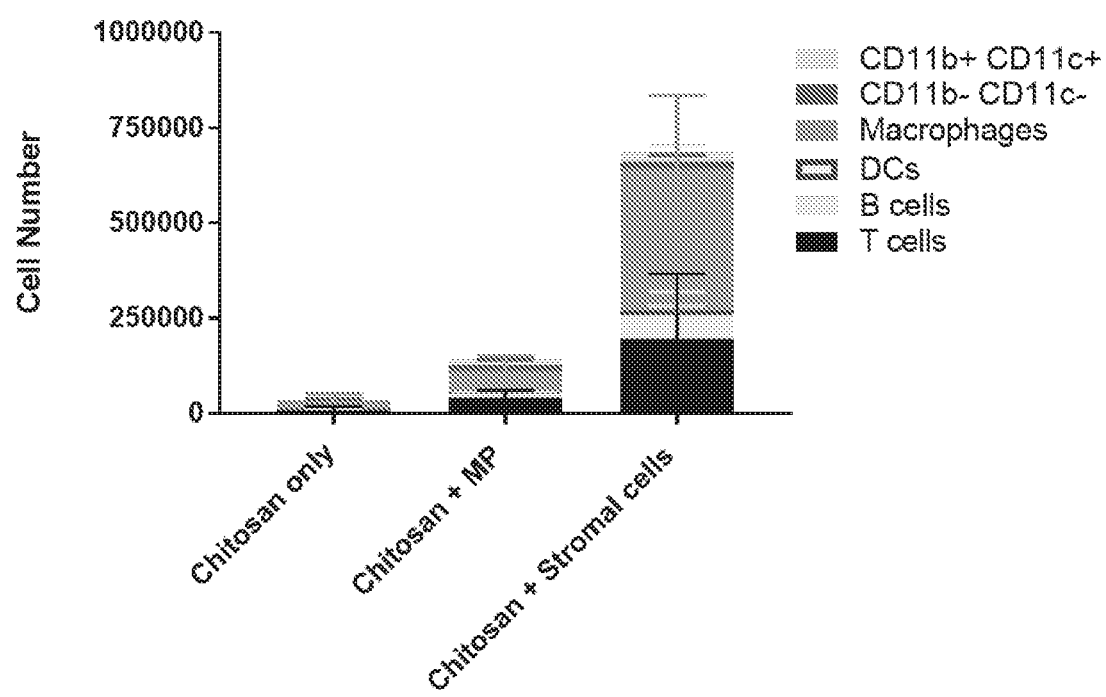
Figure 5A:
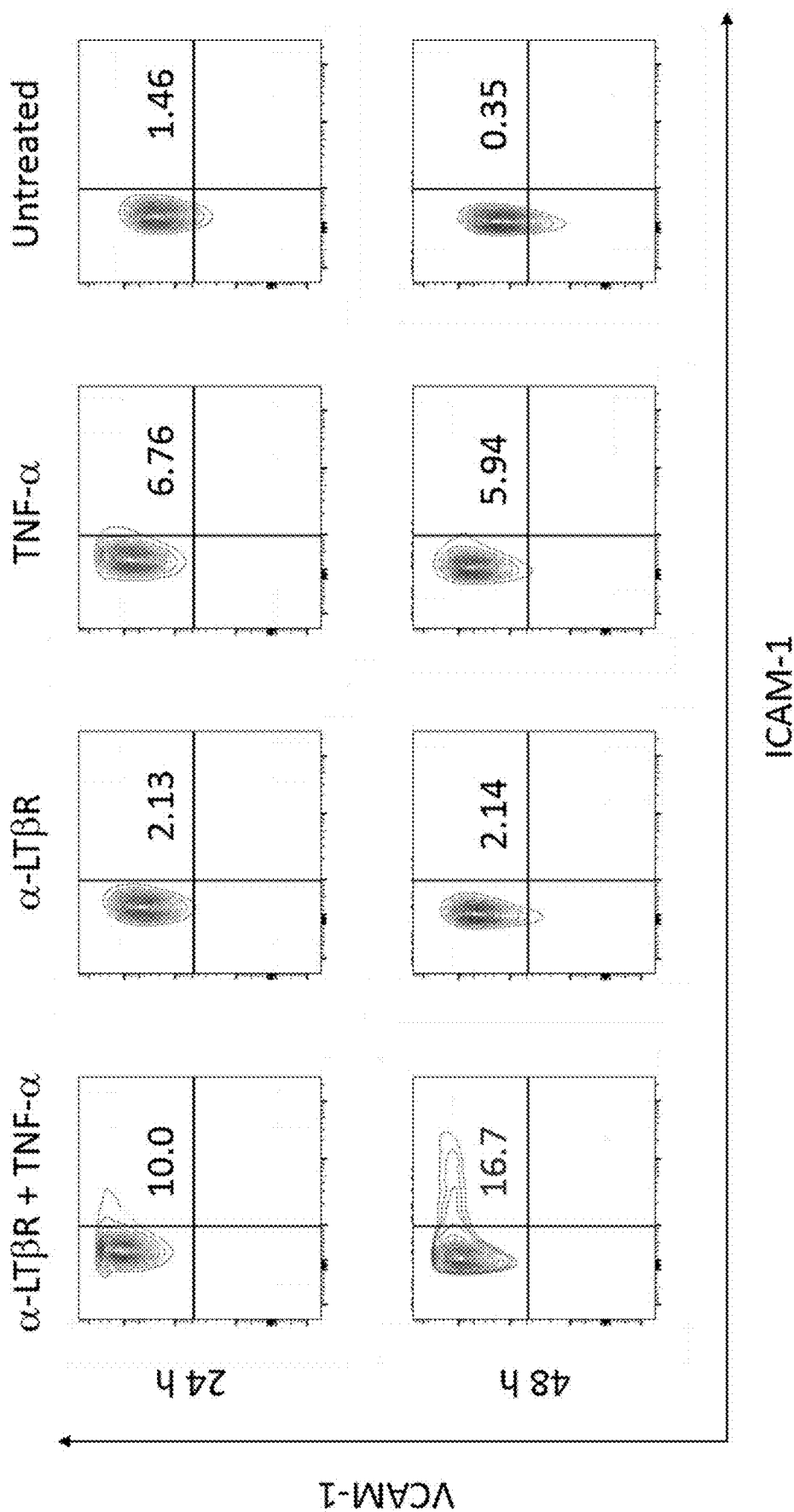
FIGS. 5A and 5B show in vitro stimulation of 1.F3 stromal cells with an agonistic lymphotoxin b receptor antibody (α-LTbR) and TNF-α.
Figure 5B:
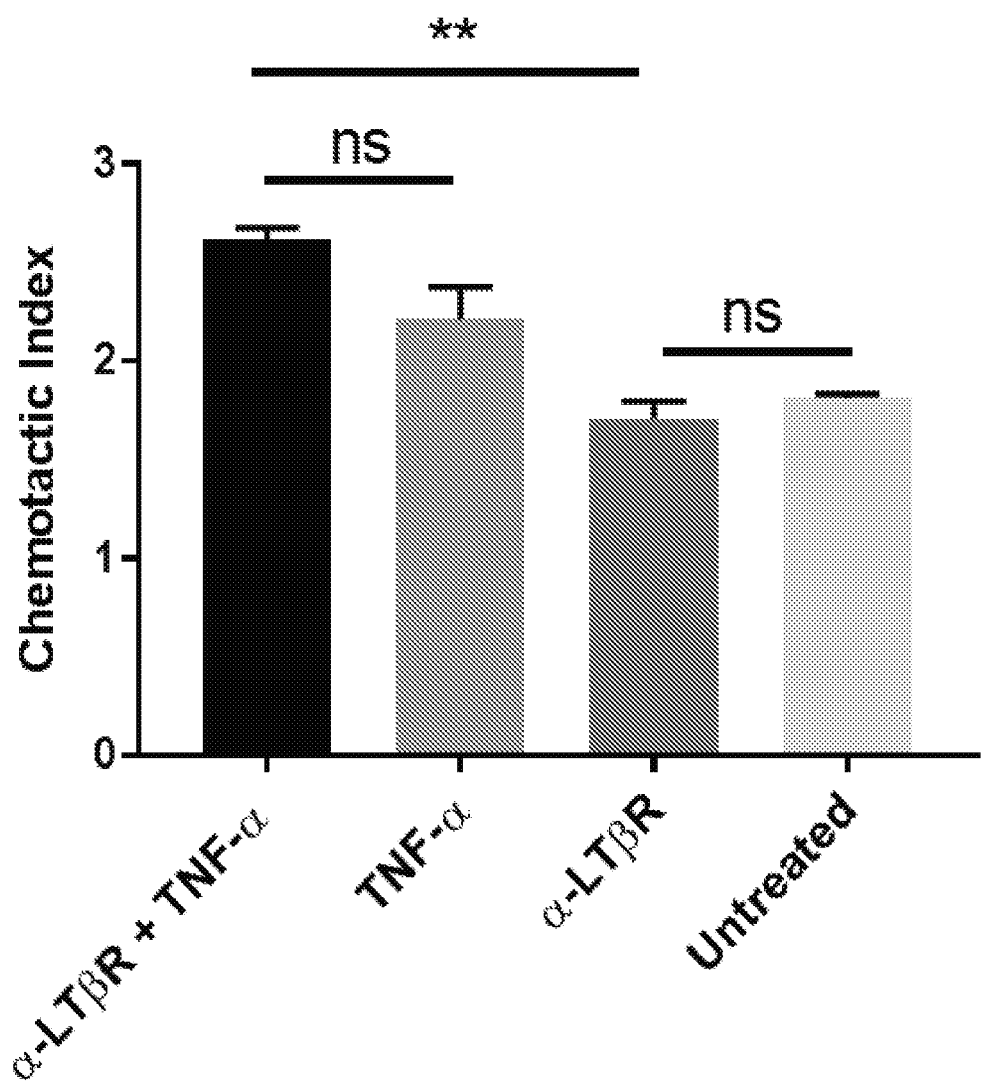
Figure 6:
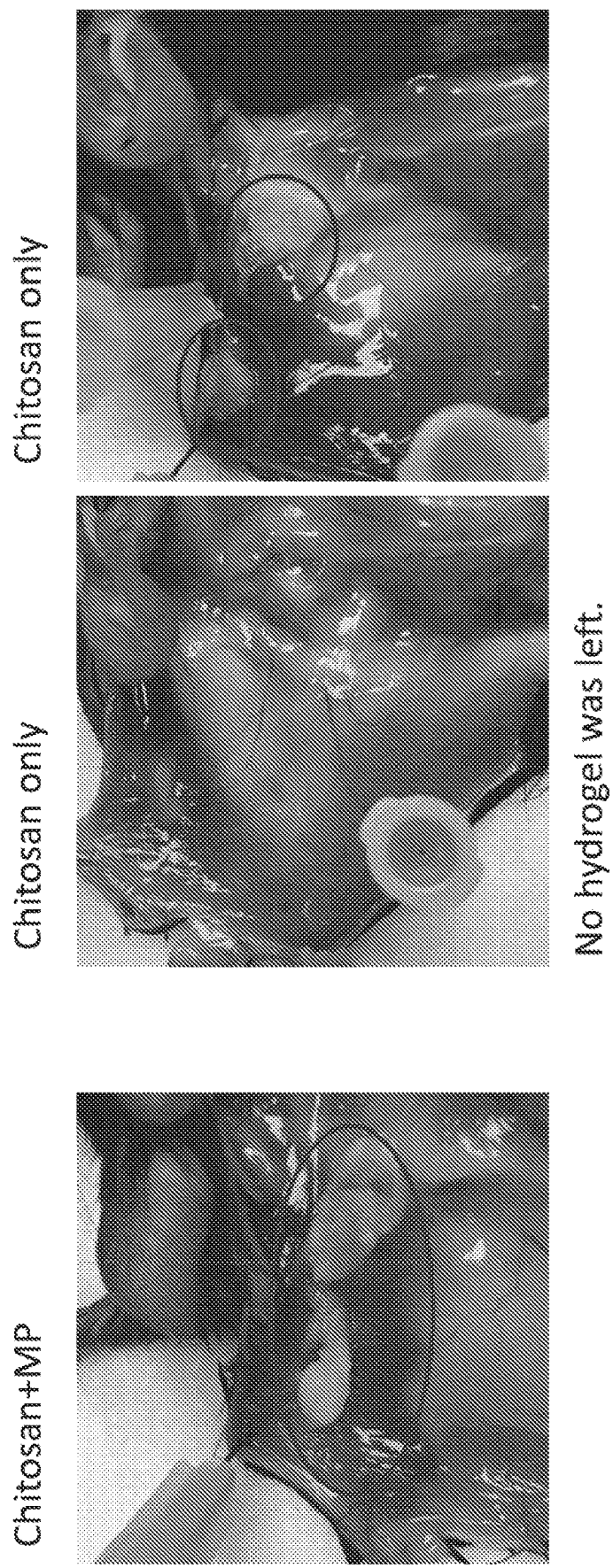
FIG. 6 contains images on day 19 showing chitosan+MP or chitosan only.
Figure 7:
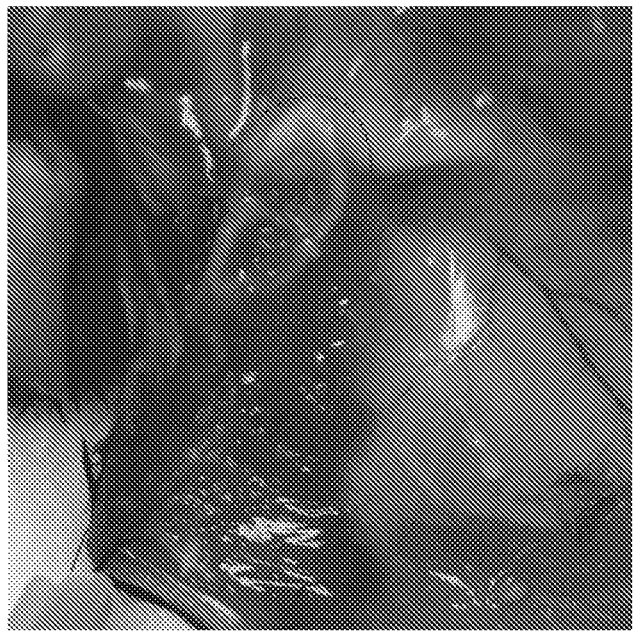
FIG. 7 contains images on day 19 showing chitosan+MP hydrogel or residual part.
Figure 7:
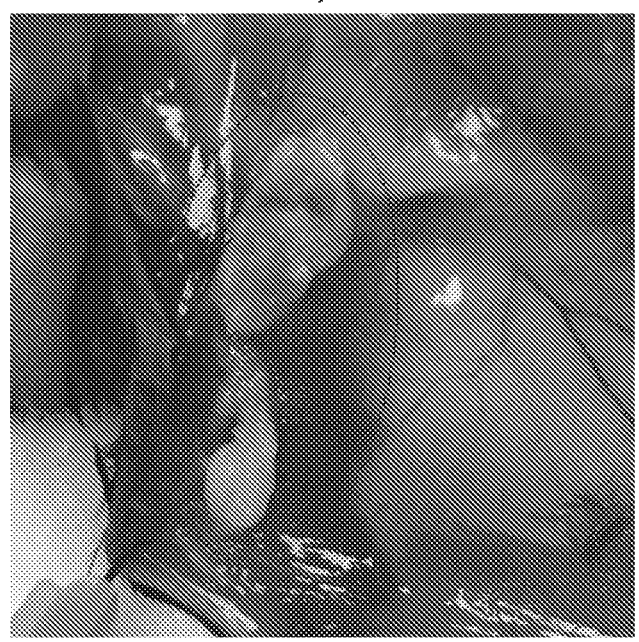
Figure 8A:
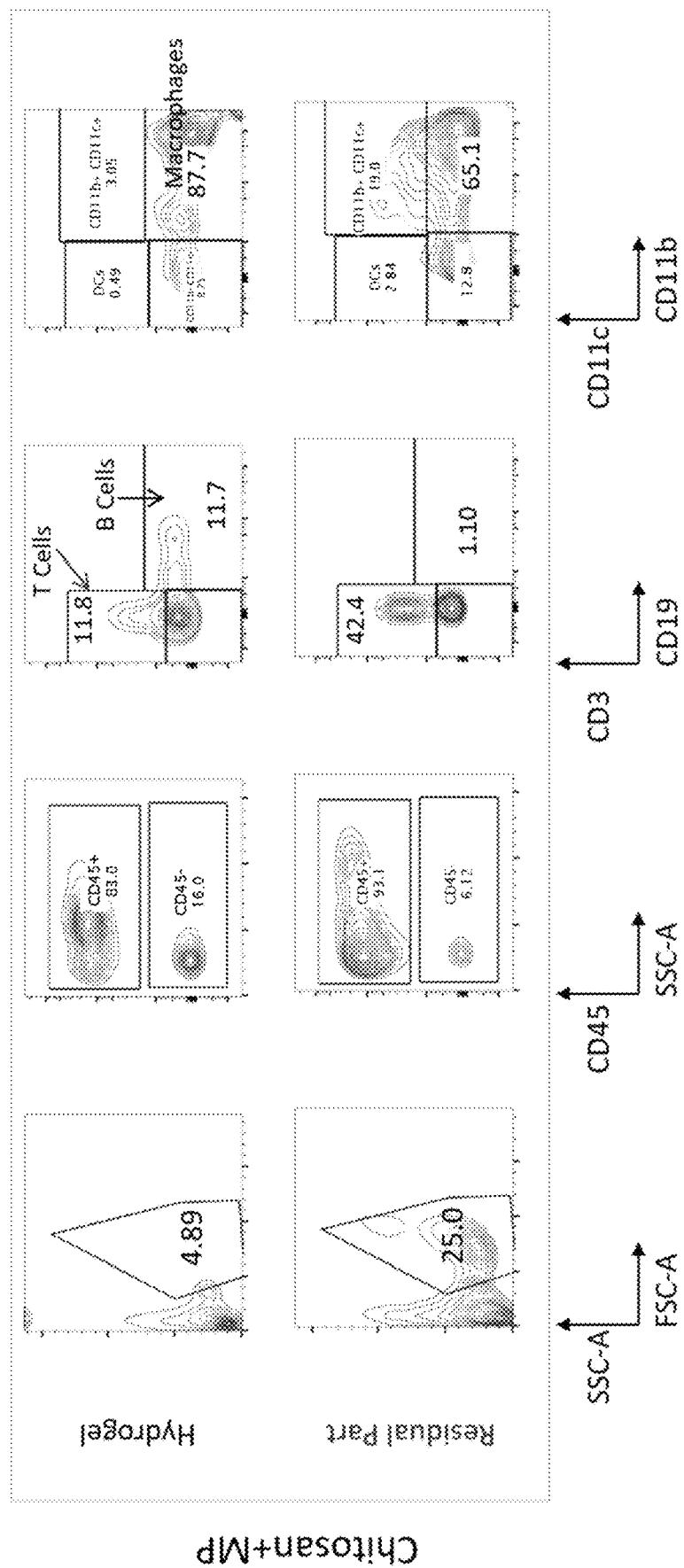
FIGS. 8A and 8B are flow cytometry images of hitosan+MP or chitosan only, hydrogel or residual part.
Figure 8B:
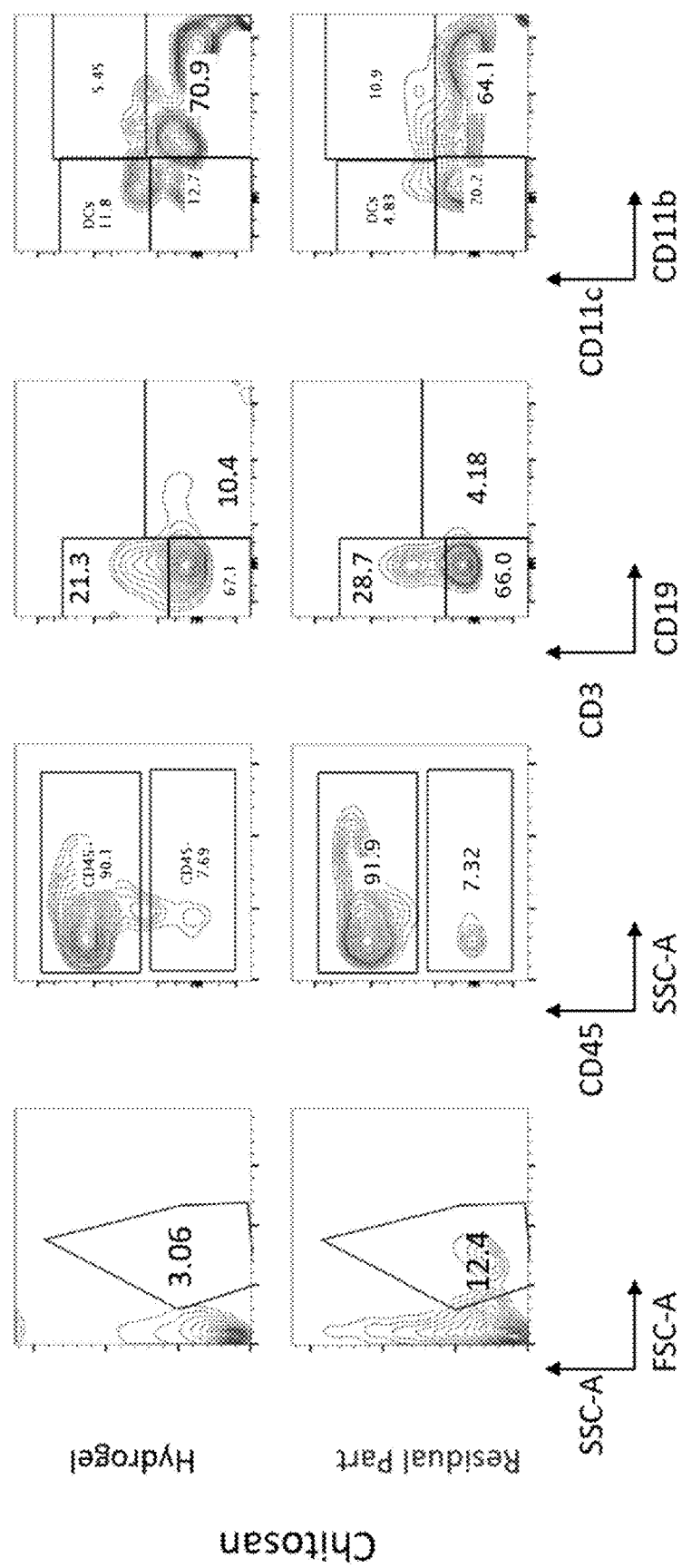
Figure 9A:
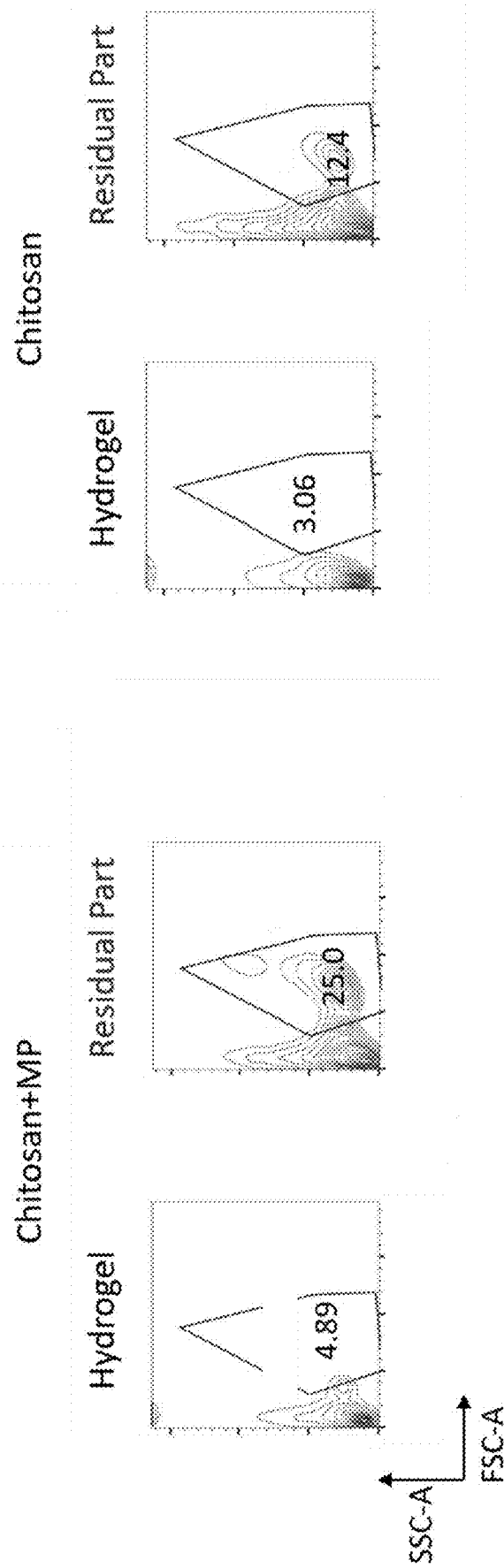
FIGS. 9A and 9B show singlet live cells infiltrated in chitosan hydrogel with and without chemokine releasing microparticles at day 19.
Figure 9B:
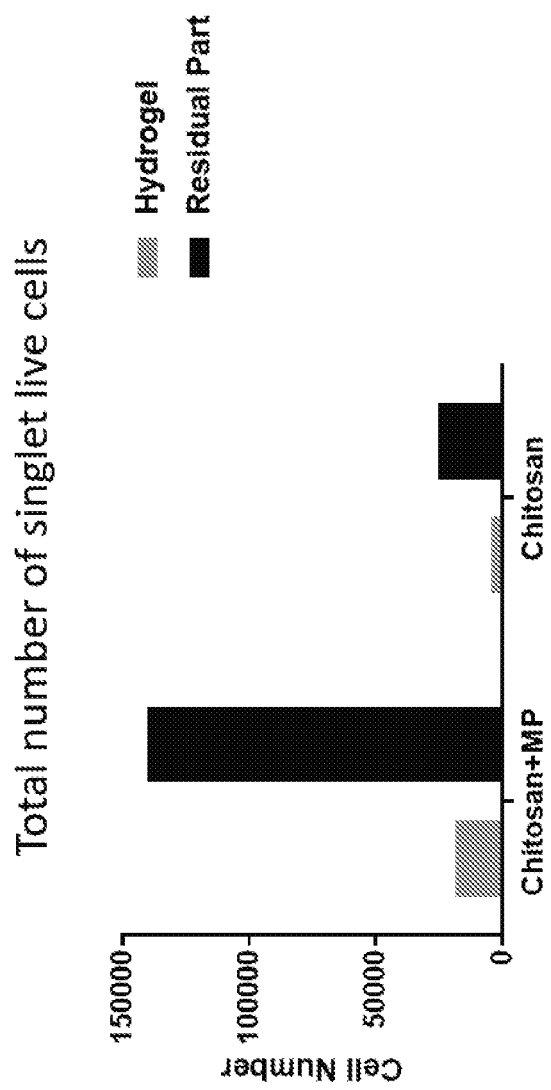
Figure 10:
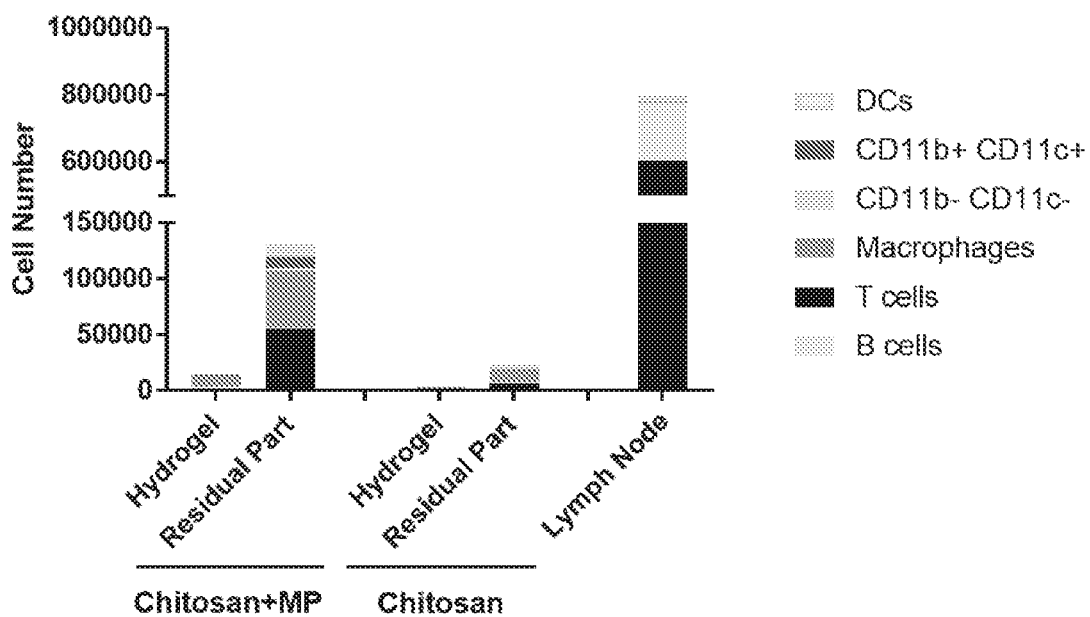
FIG. 10 shows total number of immune cells infiltrating into chitosan hydrogel with and without chemokine releasing microparticles compared to lymph node.
Figure 11:
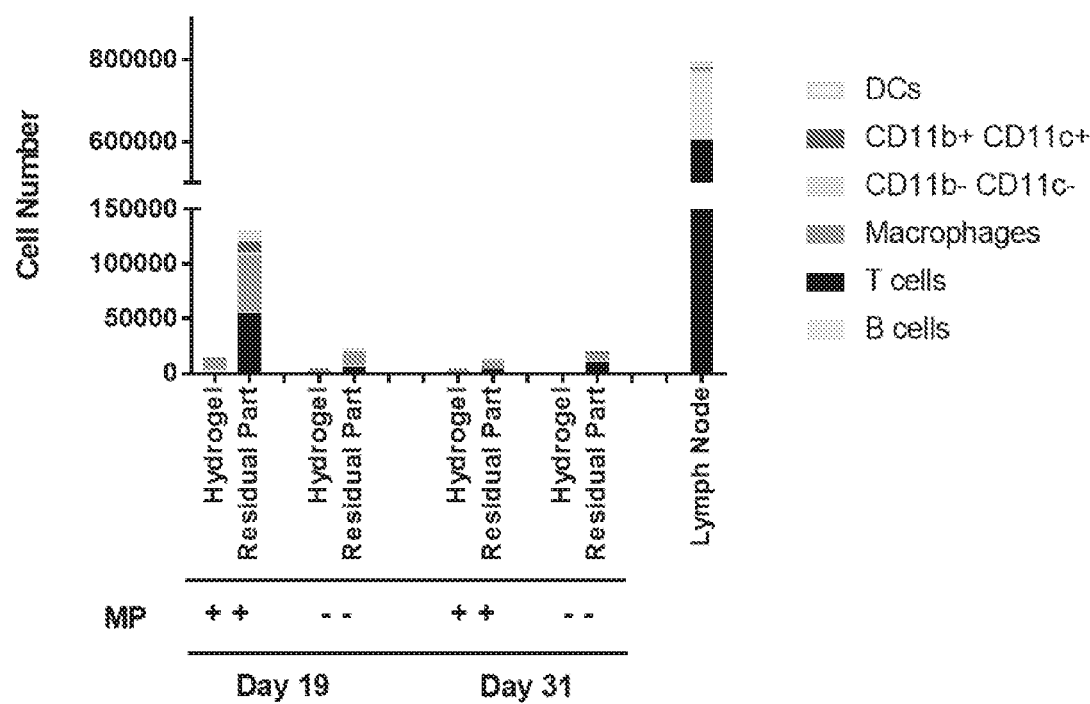
FIG. 11 shows total number of immune cells infiltrating into chitosan hydrogel with and without chemokine releasing microparticles at day 19 and day 31.
Figure 12:
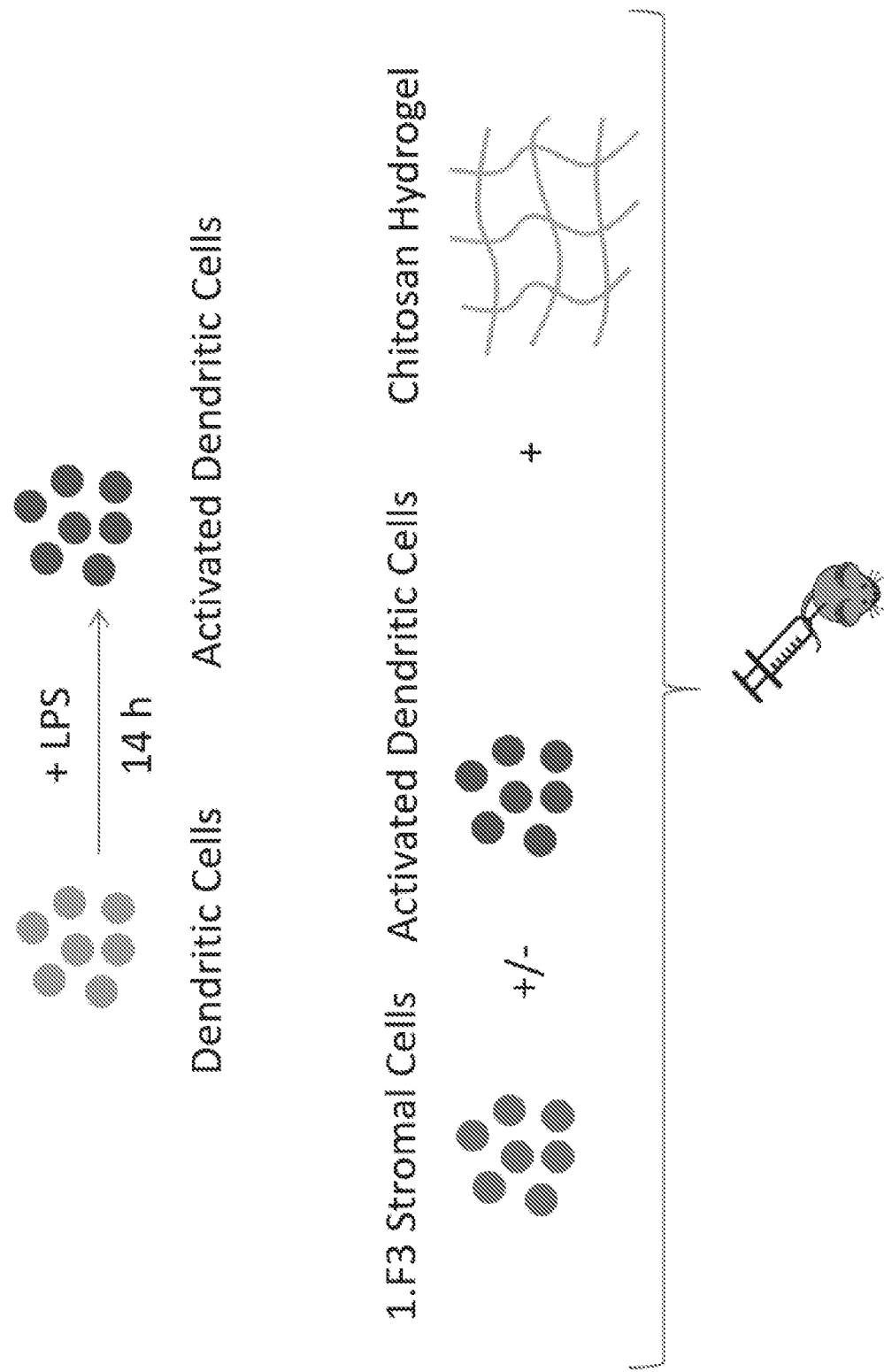
FIG. 12 shows bioengineering TLS using stromal cells and activated dendritic cells embedded in chitosan hydrogel.
Figure 13:
FIG. 13 contains images of mice treated with 1.F3 Stromal+Chitosan at day 8.
Figure 13:
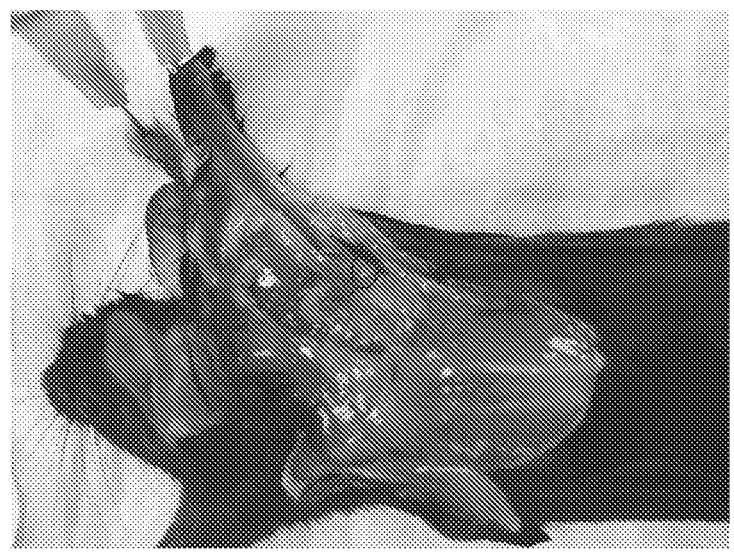
Figure 14:
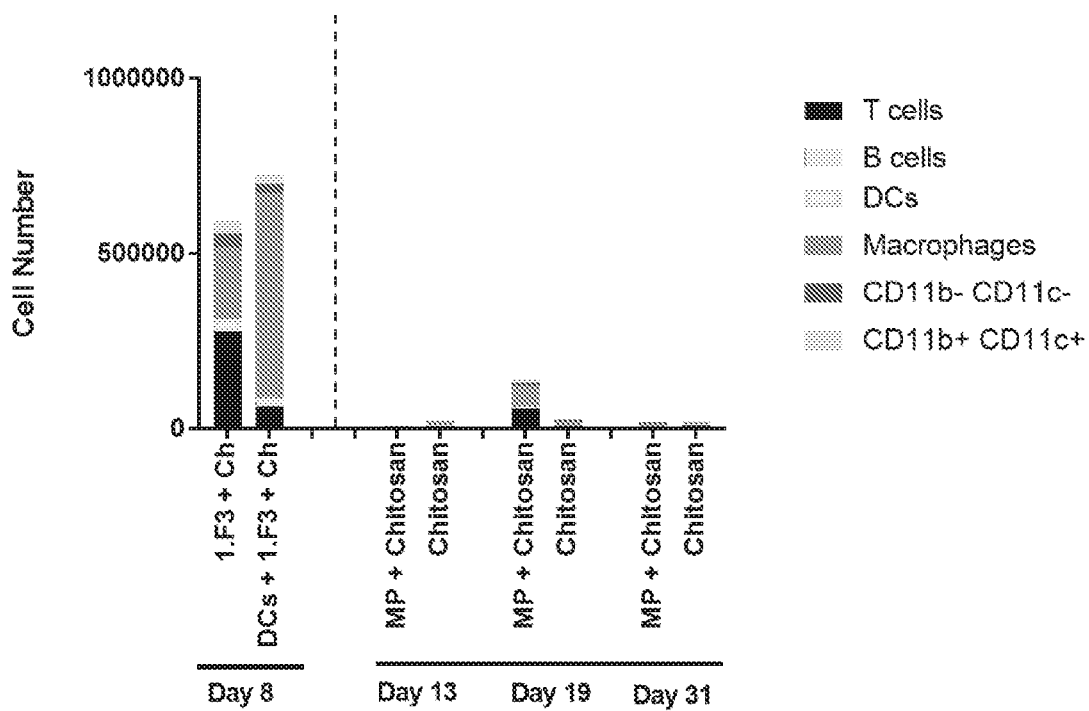
FIG. 14 shows cell number of T cells, B cells, DCs, macrophages, CD11b− CD11c−, and CD11b+CD11c+ cells after treatment with 1.F3+chitosan or DCs+1.F3+chitosan at day 8, or MP+chitosan or chitosan alone at day 13, day 19, or day 31.
Figure 15:
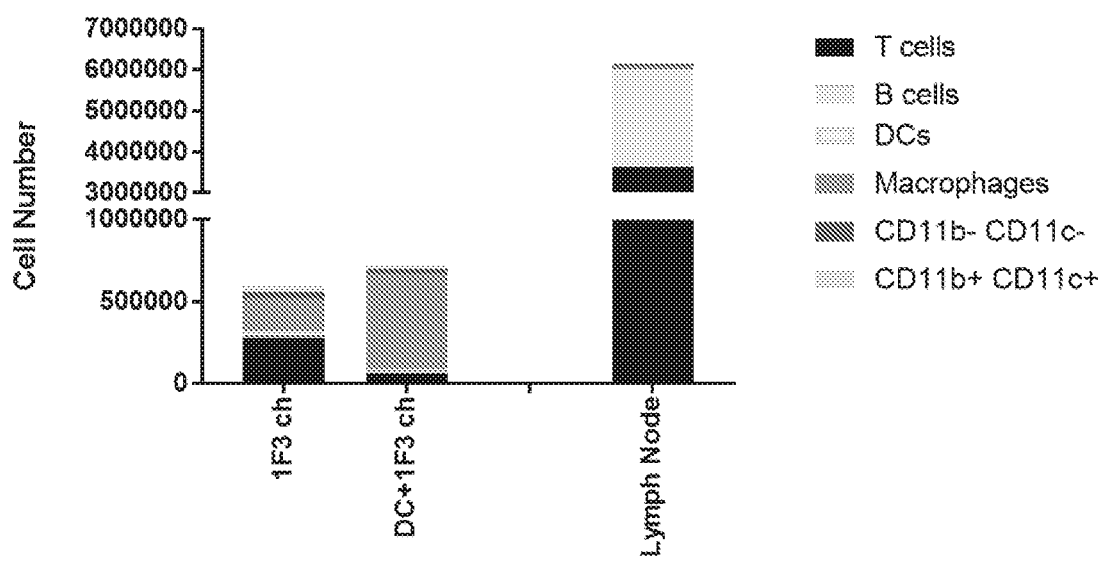
FIG. 15 shows total number of immune cells infiltrated into structures induced by 1.F3 stromal cells +/−activated DCs in chitosan hydrogel at day 8.
Figure 16B:
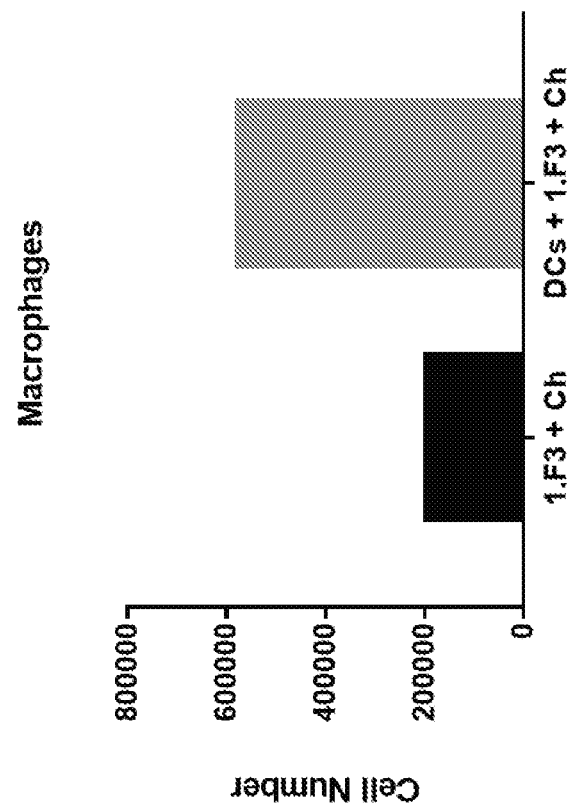
FIGS. 16A to 16D show total number of immune cells infiltrated into structures induced by 1.F3 stromal cells +/−activated DCs in chitosan hydrogel at day 8.
Figure 16A:
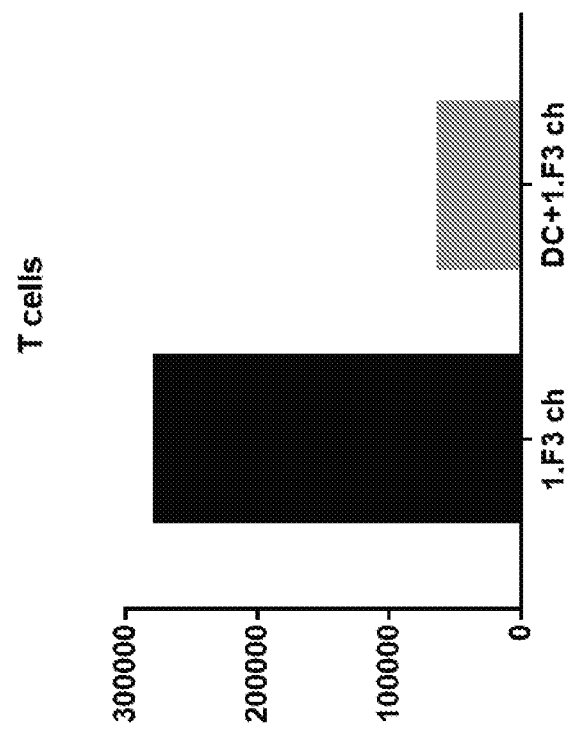
Figures 16C, 16D:
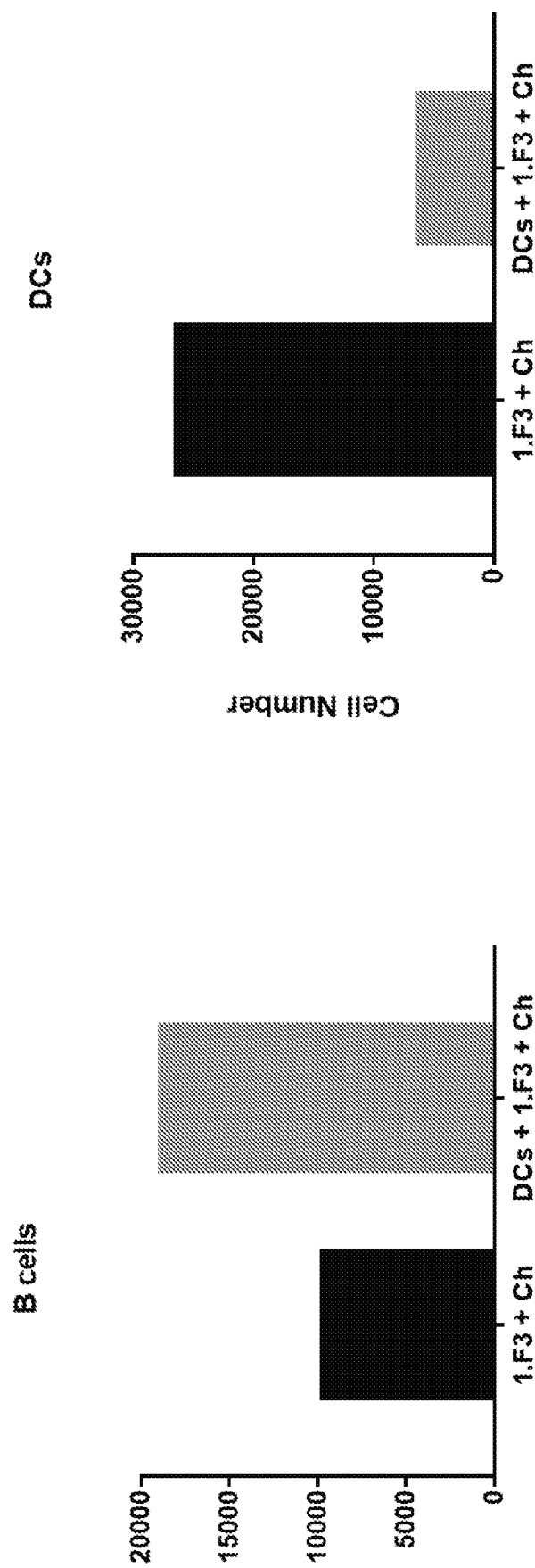
Figure 17:
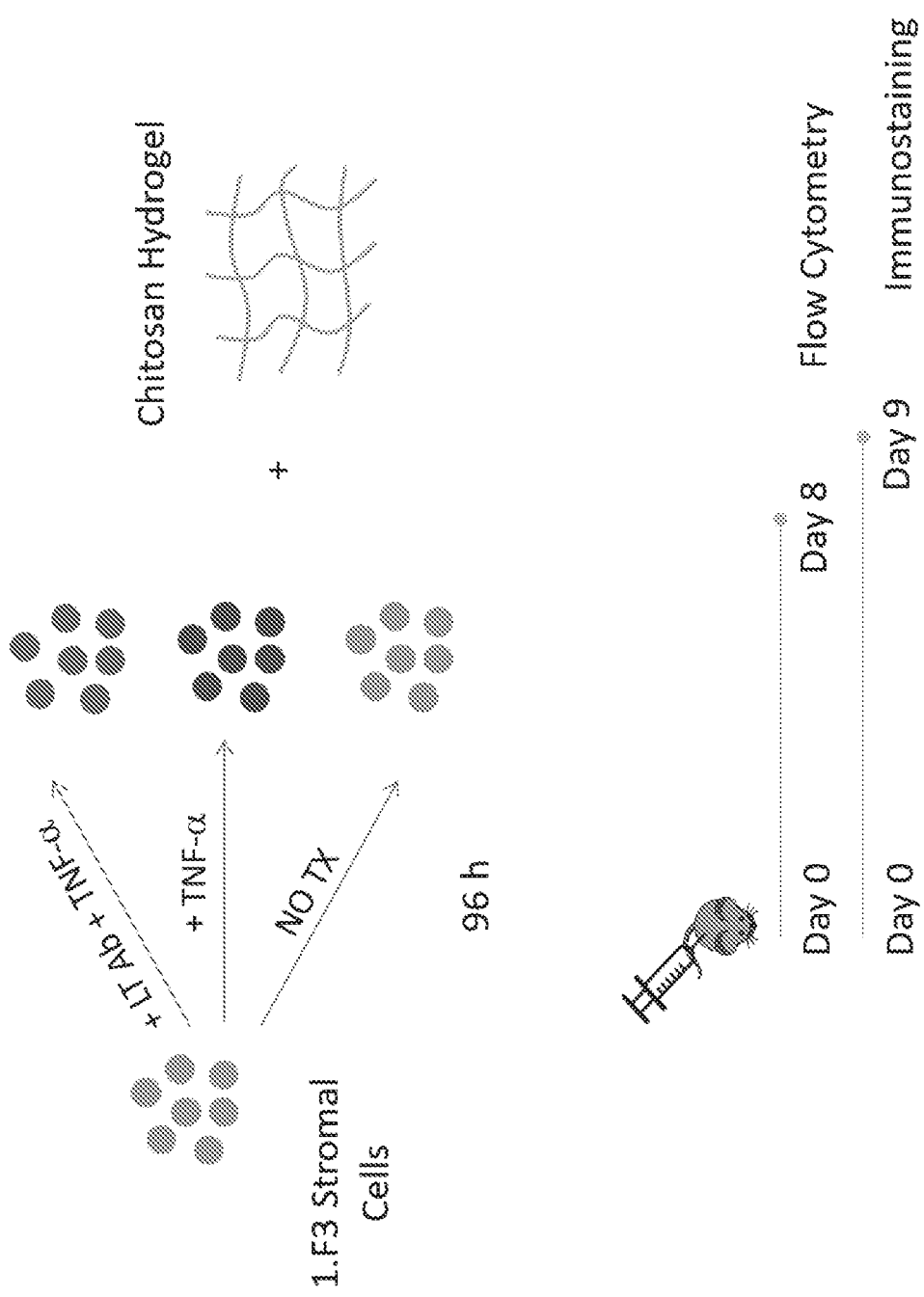
FIG. 17 shows TNF-α and/or LT Ab activated stromal cells embedded in chitosan hydrogel FIG. 18 contains images showing (1.F3 Stromal pretreated with Lymphotoxin Ab and TNF-α)+Chitosan at day 8.
Figure 18:
Figure 18:
Figure 19:
FIG. 19 contains images showing 1.F3 Stromal cells+Chitosan at day 9.
Figure 19:
Figure 20:
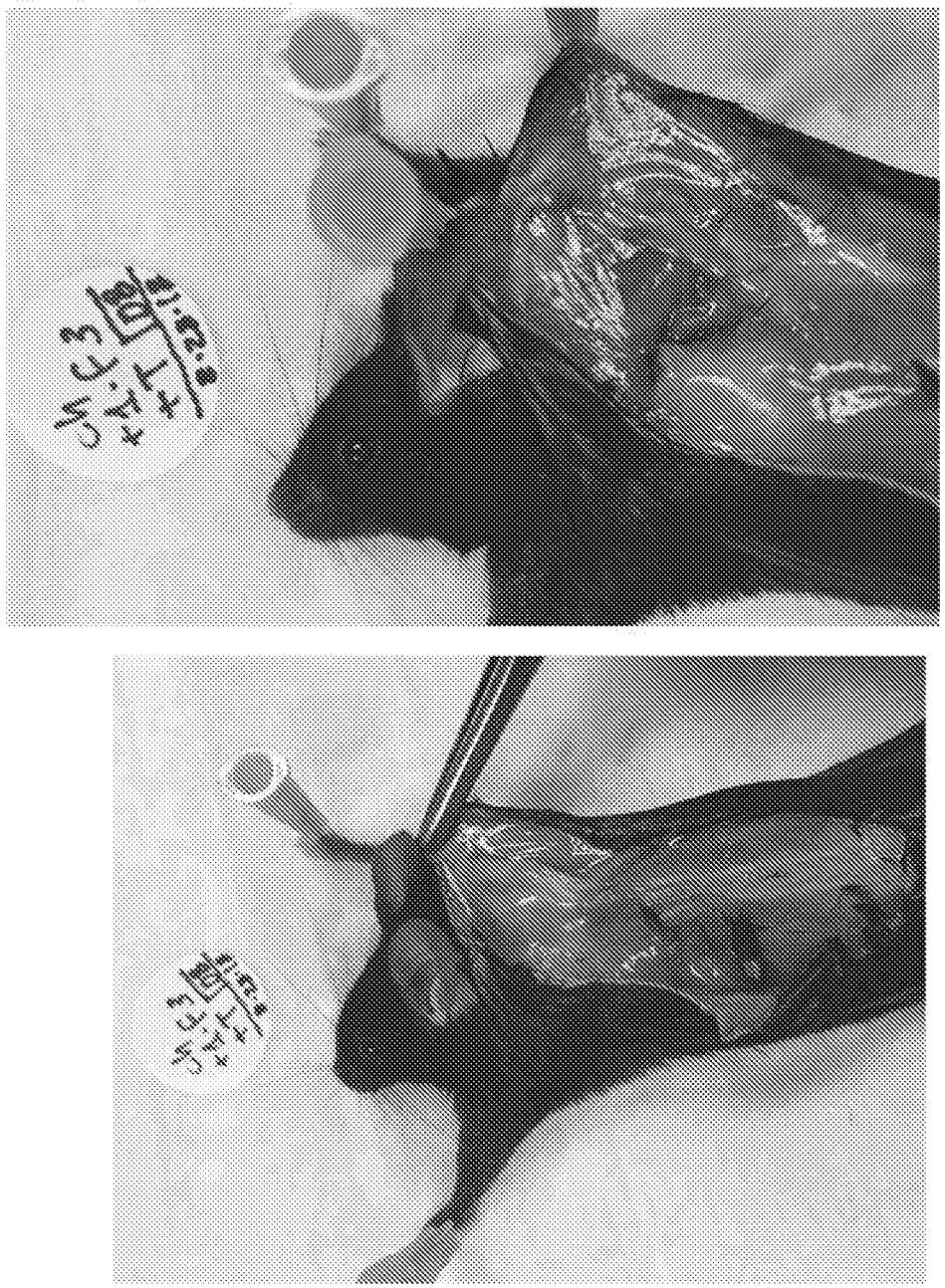
FIG. 20 contains images showing (1.F3 Stromal pretreated with TNF-α)+Chitosan at day 8.
Figure 21:
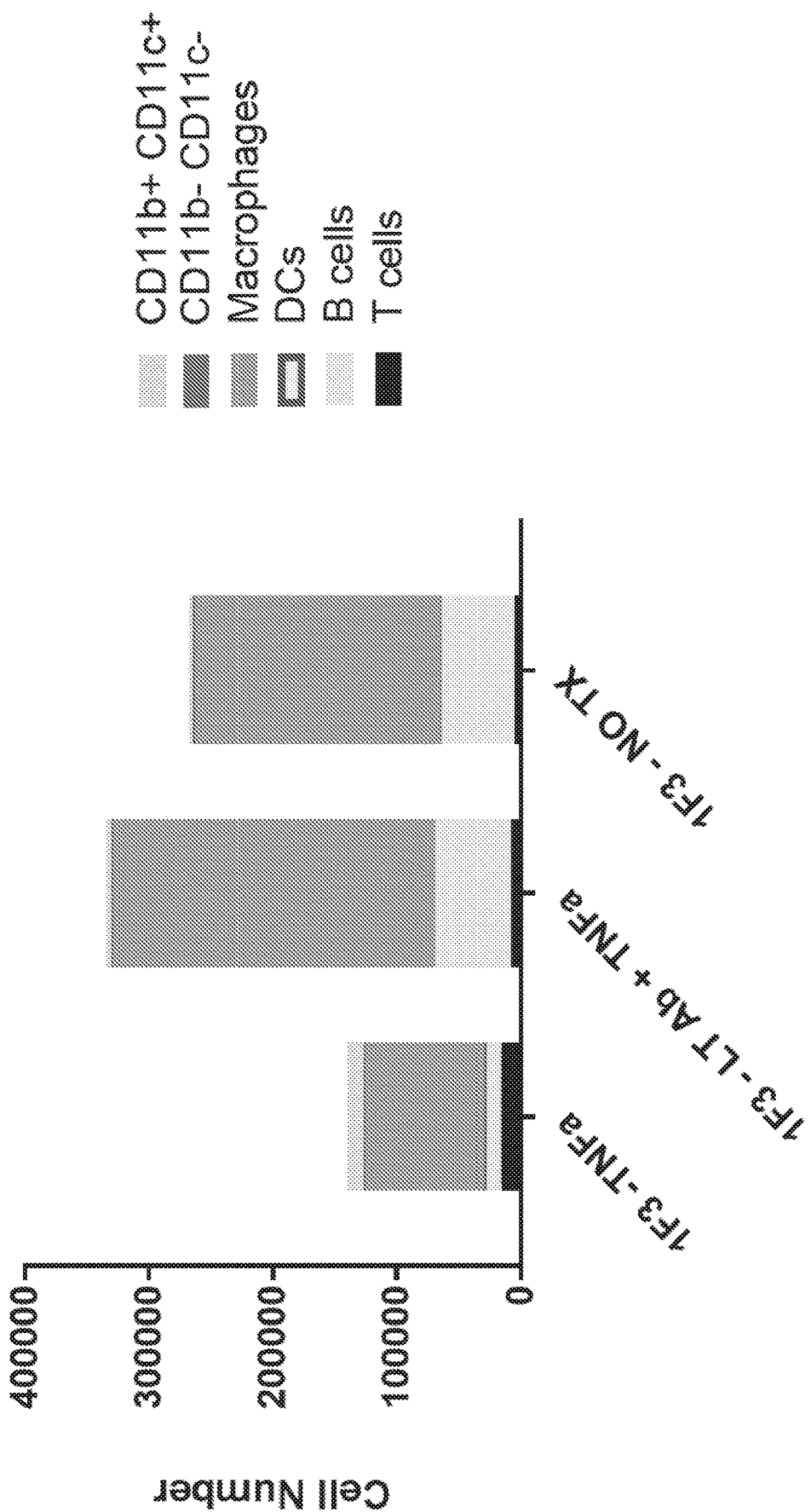
FIG. 21 shows total number of immune cells infiltrated into structures induced by 1.F3 stromal cells in chitosan hydrogel at day 8.
Figures 22A, 22B:
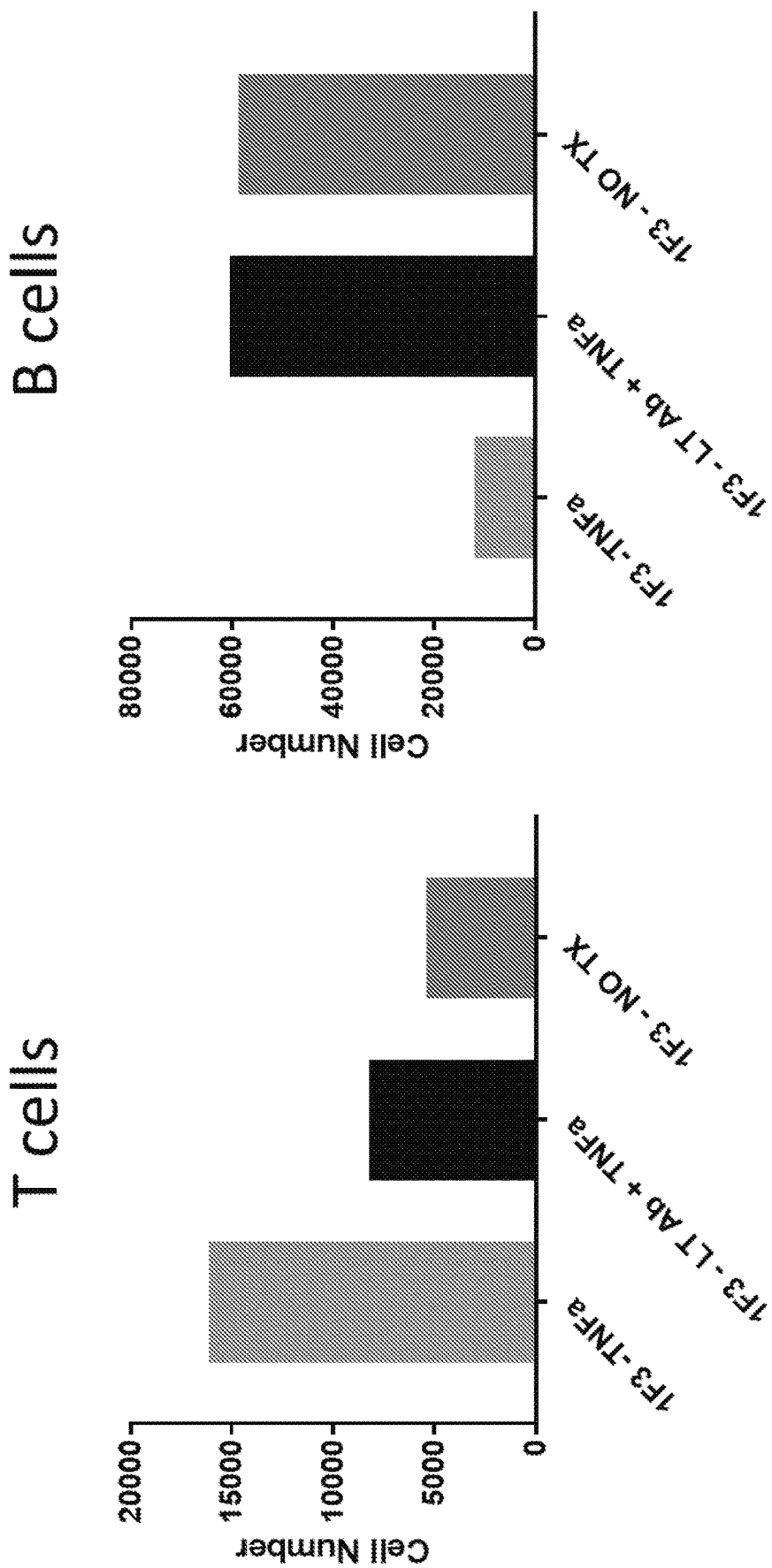
FIGS. 22A to 22D are bar graphs showing total cell number of different immune cell populations infiltrated in chitosan hydrogel containing stromal cells with and without ex vivo stimulation with TNF-α and/or LT Ab.
Figure 22D:
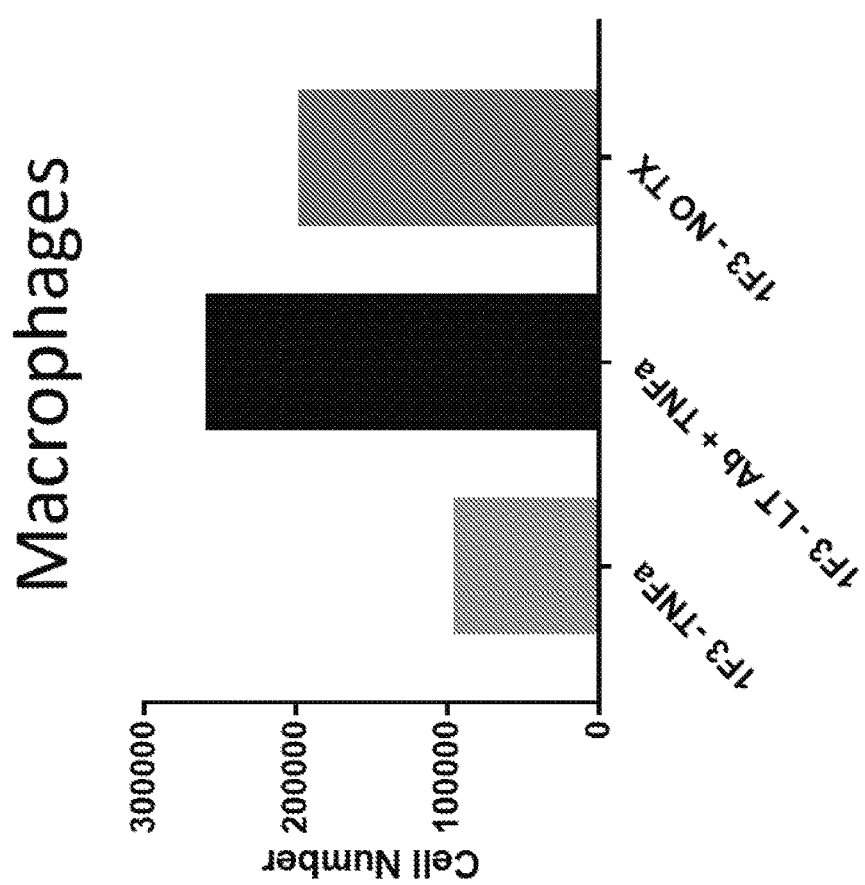
Figure 22C:
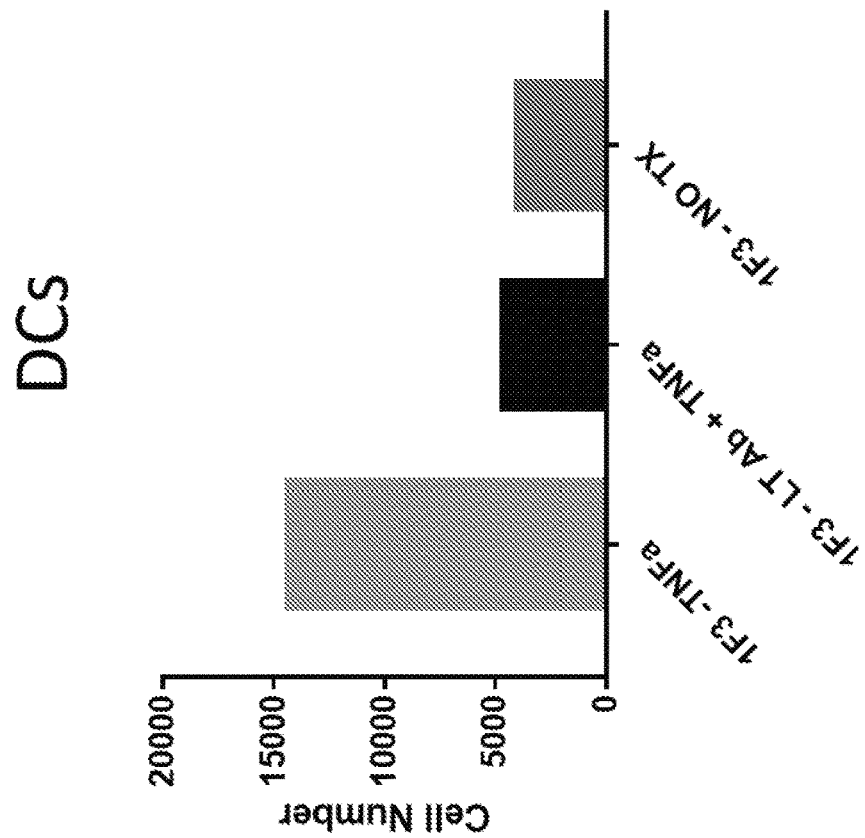
Figure 23:
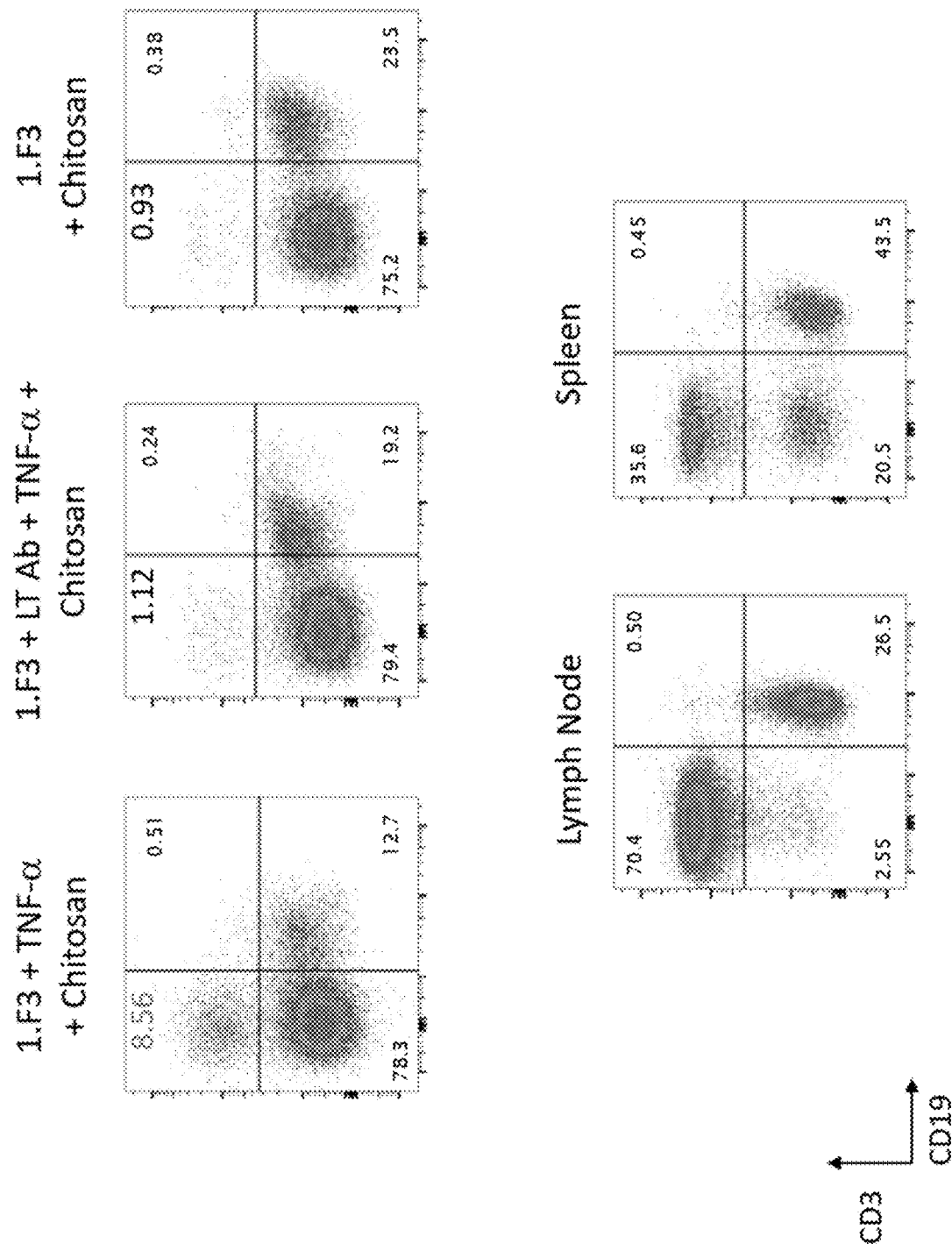
FIG. 23 shows ex vivo stimulation of 1.F3 stromal cells with TNF-α results in better recruitment of T cells.

Results are shown in FIGS. 1 to 5. Chemokine-releasing microparticles in chitosan resulted in 4-fold higher infiltration of T cells compared to the chitosan control. Although being higher in number compared to the control, relatively small numbers of B cells were attracted into these structures. When stromal cells were used in chitosan hydrogel, the structures contained more than 6-fold increased numbers of CD45+ cells compared to chemokine-releasing microparticles in chitosan. These CD45+ cells included 30.9% T, 9.6% B, and 6.2% dendritic cells and 50.1% macrophages.

CONCLUSIONS

Chitosan hydrogels with chemokine-releasing microparticles or stromal cells have potential in inducing TLSs in mice. Findings suggest that stromal cells are essential for the recruitment and organization of lymphocytes in TLSs.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A composition consisting of CCL19, CCL21, CXCL13, and lymphotoxin-alpha2/beta1 encapsulated in lipid-enveloped mesoporous microparticles embedded in a thermosensitive chitosan hydrogel.

2. A method for bioengineering tertiary lymphoid structures (TLSs) in animals, comprising administering to the animal the composition of claim 1.

3. A method for treating a solid tumor in a subject, comprising administering an effective amount of the composition of claim 1 to the solid tumor.

4. The method of claim 3, wherein the composition is implanted into the solid tumor.

5. A method for enhancing immunotherapy in a subject with a solid tumor, comprising administering to the subject an effective amount of the composition of claim 1 to the solid tumor.

6. The method of claim 5, wherein the composition is implanted into the solid tumor.

7. The method of claim 5, wherein the immunotherapy comprises adoptive transfer of a therapeutic lymphocyte.

8. The method of claim 5, wherein the immunotherapy comprises a checkpoint inhibitor selected from the group consisting of an anti-PD-1 antibody, an anti-PD-L1 antibody, and an anti-CTLA-4 antibody.

* * * * *